(12) United States Patent
Hagiwara

(10) Patent No.: US 7,173,997 B2
(45) Date of Patent: Feb. 6, 2007

(54) X-RAY CT IMAGING METHOD AND X-RAY CT APPARATUS

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/979,534

(22) Filed: Nov. 2, 2004

(65) Prior Publication Data

US 2005/0094761 A1    May 5, 2005

(30) Foreign Application Priority Data

Nov. 4, 2003 (JP) ............... 2003-373855

(51) Int. Cl.
*A61B 6/00* (2006.01)
(52) U.S. Cl. .......................... 378/15; 378/901
(58) Field of Classification Search ............... 378/4, 378/15, 20, 62, 901
See application file for complete search history.

(56) References Cited

U.S. PATENT DOCUMENTS

| | | | |
|---|---|---|---|
| 5,612,985 A * | 3/1997 | Toki et al. ............... | 378/4 |
| 5,991,356 A | 11/1999 | Horiuchi et al. | |
| 6,061,421 A | 5/2000 | Hagiwara | |
| 6,301,325 B1 | 10/2001 | Besson et al. | |
| 6,430,253 B1 * | 8/2002 | Oikawa ............... | 378/15 |
| 6,442,228 B1 | 8/2002 | Woloschek et al. | |
| 6,445,764 B2 | 9/2002 | Gohno et al. | |
| 6,463,118 B2 | 10/2002 | Besson | |
| 6,539,074 B1 | 3/2003 | Yavuz et al. | |
| 6,650,727 B2 | 11/2003 | Kuroda | |
| 6,744,844 B2 | 6/2004 | Horiuchi | |
| 6,795,522 B2 | 9/2004 | Nishide et al. | |
| 2003/0031290 A1 | 2/2003 | Sugihara et al. | |
| 2005/0008116 A1 | 1/2005 | Nishide et al. ............... | 378/20 |

FOREIGN PATENT DOCUMENTS

| | | |
|---|---|---|
| JP | 08-173413 | 7/1996 |
| JP | 2002-066420 | 3/2002 |
| JP | 2002-147061 | 5/2002 |
| JP | 2002-147231 | 5/2002 |
| JP | 2002-235561 | 8/2002 |
| JP | 2002-235662 | 8/2002 |
| JP | 2002-267833 | 9/2002 |
| JP | 2002-322756 | 11/2002 |
| JP | 2002-338947 | 11/2002 |

OTHER PUBLICATIONS

European Patent Office Search Report; 156283/10321; 04256824.6-2305-; GE Medical Systems Global Technology Company LLC; 3 pgs.

* cited by examiner

*Primary Examiner*—Courtney Thomas
(74) *Attorney, Agent, or Firm*—Carl B. Horton, Esq.; Armstrong Teasdale LLP

(57) ABSTRACT

A method of reducing the distance of rectilinear motion in a helical scan includes defining a rectilinear motion start point La and a rectilinear motion end point Lb within a region of interest ROI for which a CT image is to be created, collecting projection data from the rectilinear motion start point La to the rectilinear motion end point Lb, and creating a CT image at a desired image position in the region of interest ROI using the collected projection data.

19 Claims, 18 Drawing Sheets

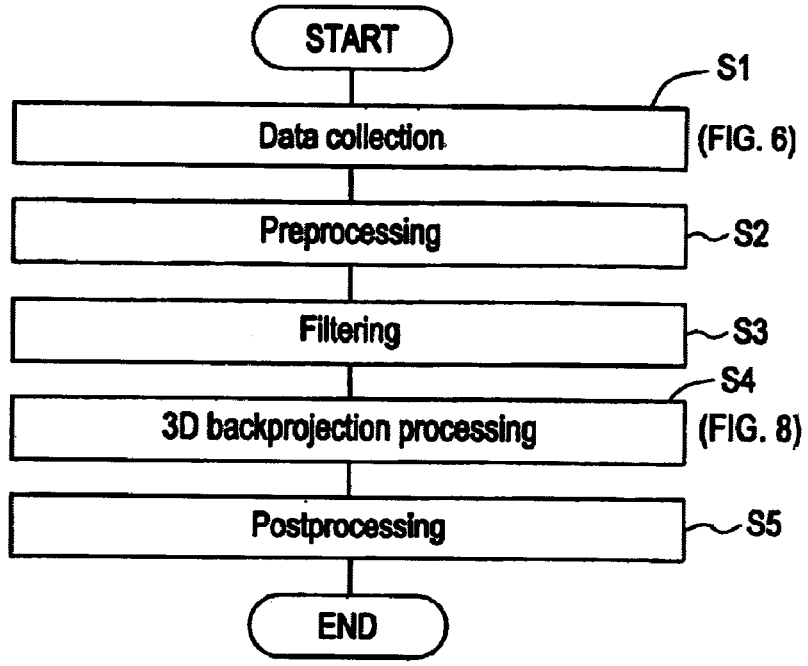

X-RAY CT IMAGING METHOD AND X-RAY CT APPARATUS

CROSS REFERENCE TO RELATED APPLICATIONS

This application claims the benefit of Japanese Application No. 2003-373892 filed Nov. 4, 2003.

BACKGROUND OF THE INVENTION

The present invention relates to an X-ray CT (computed tomography) imaging method and an X-ray CT apparatus, and more particularly to an X-ray CT imaging method and an X-ray CT apparatus by which the distance of rectilinear motion in a helical scan can be reduced.

As shown in FIG. 29, there is known an X-ray CT apparatus that ensures a constant speed of rectilinear motion in a region of interest ROI by controlling rectilinear motion of a table, the control comprising: appending an acceleration section A before a front end position Ra of the region of interest ROI for which an CT image is to be created to define a rectilinear motion start point La; appending a deceleration section B after a back end position Rb of the region of interest ROI to define a rectilinear motion end point Lb; starting rectilinear motion of the table at a table position at which an X-ray tube 21 looks straight down on the rectilinear motion start point La; increasing the speed of rectilinear motion in the acceleration section A, driving rectilinear motion at a constant speed in the region of interest ROI and decreasing the speed of rectilinear motion in the deceleration section B; and stopping rectilinear motion at a table position at which the X-ray tube 21 looks straight down on the rectilinear motion end point Lb (see Patent Document 1, for example).

It should be noted that in general, the table is rectilinearly moved while rotating the X-ray tube 21 and multi-row detector 24 around a subject to be imaged in a helical scan, although for convenience of illustration FIG. 29 represents the rectilinear motion as if it occurred without rotating the X-ray tube 21 and multi-row detector 24.

[Patent Document 1]Japanese Patent Application Laid Open No. H8-173413.

As can be seen from FIG. 29, the conventional technique appends the acceleration section A before the region of interest ROI and the deceleration section B after the region of interest ROI.

This, however, leads to a problem that the range of rectilinear motion L is longer than the region of interest ROI. Thus, if reciprocal rectilinear motion is conducted, the cycle time becomes longer. Moreover, if X-rays are constantly emitted during rectilinear motion, the exposure dose increases.

SUMMARY OF THE INVENTION

It is therefore an object of the present invention to provide an X-ray CT imaging method and an X-ray CT apparatus by which the distance of rectilinear motion in a helical scan can be reduced.

In its first aspect, the present invention provides an X-ray CT imaging method for conducting a helical scan for collecting projection data while making relative rotation of at least one of an X-ray tube and a multi-row detector around a subject to be imaged and making relative rectilinear motion of them with respect to the subject to be imaged, said method characterized in comprising: defining a rectilinear motion start point and a rectilinear motion end point within a region of interest (ROI) for which a CT image is to be created; collecting projection data from said rectilinear motion start point to said rectilinear motion end point; and producing a CT image at a desired image position in said region of interest using the collected projection data.

As used herein, the term "relative rotation" includes: for a subject to be imaged placed in between the X-ray tube and multi-row detector, rotating at least one of the X-ray tube and multi-row detector around the subject to be imaged without rotating the subject to be imaged; rotating the subject to be imaged around its axis without rotating the X-ray tube and multi-row detector; and rotating the subject to be imaged around its axis and counter-rotating at least one of the X-ray tube and multi-row detector around the subject to be imaged.

As used herein, the term "relative rectilinear motion" includes: for a subject to be imaged placed in between the X-ray tube and multi-row detector, rectilinearly moving the subject to be imaged (or the table on which the subject to be imaged is laid) without rectilinearly moving the X-ray tube and multi-row detector; rectilinearly moving the X-ray tube and multi-row detector without rectilinearly moving the subject to be imaged (or the table on which the subject to be imaged is laid); and rectilinearly moving the subject to be imaged (or the table on which the subject to be imaged is laid) and rectilinearly moving the X-ray tube and multi-row detector in the opposite direction.

According to the X-ray CT imaging method in the first aspect, a rectilinear motion start point and a rectilinear motion end point are defined within a region of interest, and projection data are collected from the rectilinear motion start point to the rectilinear motion end point. When a multi-row detector is employed, the X-ray beam covers the ROI front end even if the rectilinear motion start point is defined within the region of interest because the X-ray beam thickness in the direction of rectilinear motion is large. Similarly, the X-ray beam covers the ROI back end even if the rectilinear motion end point is defined within the region of interest. Therefore, a CT image can be created at a desired image position from the front end to the back end of the region of interest using the collected projection data. At that time, the distance of rectilinear motion can be made shorter than the region of interest. Accordingly, the imaging time can be reduced. Moreover, the cycle time for reciprocal rectilinear motion can be reduced. Furthermore, the X-ray exposure dose can be reduced.

The CT image may be created by a two-dimensional or three-dimensional image reconstruction technique.

In its second aspect, the present invention provides the X-ray CT imaging method having the aforementioned configuration, characterized in that: said rectilinear motion start point lies inward from the ROI front end position by half or approximately half of the X-ray beam thickness in the direction of rectilinear motion.

As used herein, "the X-ray beam thickness in the direction of rectilinear motion" refers to the X-ray beam thickness in the direction of rectilinear motion at the position of the subject to be imaged placed in between the X-ray tube and multi-row detector.

At a position at which the X-ray tube looks straight down on the rectilinear motion start point, the X-ray beam covers the subject to be imaged anterior to the start point by half or approximately half of the X-ray beam thickness in the direction of rectilinear motion.

According to the X-ray CT imaging method in the second aspect, the rectilinear motion start point is therefore defined inward from the ROI front end position by half or approximately half of the X-ray beam thickness in the direction of rectilinear motion.

In its third aspect, the present invention provides the X-ray CT imaging method having the aforementioned configuration, characterized in that: said rectilinear motion end point lies inward from the ROI back end position by half or about half of the X-ray beam thickness in the direction of rectilinear motion.

As used herein, "the X-ray beam thickness in the direction of rectilinear motion" refers to the X-ray beam thickness in the direction of rectilinear motion at the position of the subject to be imaged placed in between the X-ray tube and multi-row detector.

At a position at which the X-ray tube looks straight down on the rectilinear motion end point, the X-ray beam covers the subject to be imaged posterior to the end point by half or approximately half of the X-ray beam thickness in the direction of rectilinear motion.

According to the X-ray CT imaging method in the third aspect, the rectilinear motion end point is therefore defined inward from the ROI front end position by half or approximately half of the X-ray beam thickness in the direction of rectilinear motion.

In its fourth aspect, the present invention provides an X-ray CT imaging method for conducting a helical scan for collecting projection data while making relative rotation of at least one of an X-ray tube and a multi-row detector around a subject to be imaged and making relative rectilinear motion of them with respect to the subject to be imaged, said method characterized in comprising: collecting projection data from a rectilinear motion start point to a rectilinear motion end point; and creating a CT image at a desired image position in a region of interest (ROI) from an ROI front end position anterior to said rectilinear motion start point to an ROI back end position posterior to said rectilinear motion end point using the collected projection data.

As used herein, the phrase "relative rotation" includes: for a subject to be imaged placed in between the X-ray tube and multi-row detector, rotating at least one of the X-ray tube and multi-row detector around the subject to be imaged without rotating the subject to be imaged; rotating the subject to be imaged around its axis without rotating the X-ray tube and multi-row detector; and rotating the subject to be imaged around its axis and counter-rotating at least one of the X-ray tube and multi-row detector around the subject to be imaged.

As used herein, the phrase "relative rectilinear motion" includes: for a subject to be imaged placed in between the X-ray tube and multi-row detector, rectilinearly moving the subject to be imaged (or the table on which the subject to be imaged is laid) without rectilinearly moving the X-ray tube and multi-row detector; rectilinearly moving the X-ray tube and multi-row detector without rectilinearly moving the subject to be imaged (or the table on which the subject to be imaged is laid); and rectilinearly moving the subject to be imaged (or the table on which the subject to be imaged is laid) and rectilinearly moving the X-ray tube and multi-row detector in the opposite direction.

According to the X-ray CT imaging method in the fourth aspect, the ROI front end is defined anterior to the rectilinear motion start point, the ROI back end is defined posterior to the rectilinear motion end point, and projection data are collected from the rectilinear motion start point to the rectilinear motion end point. When a multi-row detector is employed, the X-ray beam covers the ROI front end even if the ROI front end is defined anterior to the rectilinear motion start point because the X-ray beam thickness in the direction of rectilinear motion is large. Similarly, the X-ray beam covers the ROI back end even if the ROI back end is defined posterior to the rectilinear motion end point. Therefore, a CT image can be created at a desired image position from the ROI front end to the ROI back end using the collected projection data. At that time, the distance of rectilinear motion can be made shorter than the region of interest. Accordingly, the imaging time can be reduced. Moreover, the cycle time for reciprocal rectilinear motion can be reduced. Furthermore, the X-ray exposure dose can be reduced.

In its fifth aspect, the present invention provides the X-ray CT imaging method having the aforementioned configuration, characterized in that: said ROI front end position lies anterior to said rectilinear motion start point by half or approximately half of the X-ray beam thickness in the direction of rectilinear motion.

As used herein, "the X-ray beam thickness in the direction of rectilinear motion" refers to the X-ray beam thickness in the direction of rectilinear motion at the position of the subject to be imaged placed in between the X-ray tube and multi-row detector.

At a position at which the X-ray tube looks straight down on the rectilinear motion start point, the X-ray beam covers the subject to be imaged anterior to the start point by half or approximately half of the X-ray beam thickness in the direction of rectilinear motion.

According to the X-ray CT imaging method in the fifth aspect, the ROI front end position is therefore defined anterior to the rectilinear motion start point by half or approximately half of the X-ray beam thickness in the direction of rectilinear motion.

In its sixth aspect, the present invention provides the X-ray CT imaging method having the aforementioned configuration, characterized in that: said ROI back end position lies posterior to said rectilinear motion end point by half or approximately half of the X-ray beam thickness in the direction of rectilinear motion.

As used herein, "the X-ray beam thickness in the direction of rectilinear motion" refers to the X-ray beam thickness in the direction of rectilinear motion at the position of the subject to be imaged placed in between the X-ray tube and multi-row detector.

At a position at which the X-ray tube looks straight down on the rectilinear motion end point, the X-ray beam covers the subject to be imaged posterior to the end point by half or approximately half of the X-ray beam thickness in the direction of rectilinear motion.

According to the X-ray CT imaging method in the sixth aspect, the ROI back end is therefore defined posterior to the rectilinear motion end point by half or approximately half of the X-ray beam thickness in the direction of rectilinear motion.

In its seventh aspect, the present invention provides the X-ray CT imaging method having the aforementioned configuration, characterized in comprising making reciprocal relative rectilinear motion by: making motion from said rectilinear motion start point to said rectilinear motion end point; then re-defining said rectilinear motion start point and said rectilinear motion end point as a new rectilinear motion end point and a new rectilinear motion start point, respectively; and making relative rectilinear motion in an opposite direction.

According to the X-ray CT imaging method in the seventh aspect, since the distance of rectilinear motion can be made shorter than the region of interest, the cycle time for reciprocal relative rectilinear motion can be reduced. Thus, temporal resolution at the same image position can be improved. The invention of this aspect is especially suitable for perfusion CT.

In its eighth aspect, the present invention provides the X-ray CT imaging method having the aforementioned configuration, characterized in comprising: collecting projection data while making said relative rotation at said rectilinear motion start point without making said relative rectilinear motion; reconstructing a CT image using the collected projection data; and starting said relative rectilinear motion based on a change in said CT image.

According to the X-ray CT imaging method of the eighth aspect, since the distance of rectilinear motion is made shorter than the region of interest, the rectilinear motion start point is brought closer to the ROI center. Thus, the change in a CT image that triggers start of relative rectilinear motion can be accurately ascertained. The invention of this aspect is especially suitable for Smart Prep (GE) or Real Prep (Toshiba).

In its ninth aspect, the present invention provides the X-ray CT imaging method having the aforementioned configuration, characterized in comprising: creating a CT image by a three-dimensional image reconstruction technique.

According to the X-ray CT imaging method in the ninth aspect, since image reconstruction is performed according to a three-dimensional image reconstruction technique, artifacts caused by a large cone angle are prevented.

Known three-dimensional image reconstruction techniques include the Feldkamp method and the weighted Feldkamp method.

In its tenth aspect, the present invention provides the X-ray CT imaging method having the aforementioned configuration, characterized in that said three-dimensional image reconstruction technique is a three-dimensional back-projection method comprising: ordering the collected projection data based on the z-position of each view and extracting projection data corresponding to one line or a plurality of parallel lines at spacings of a plurality of pixels on an image reconstruction field; generating projection line data by multiplying said projection data by a cone beam reconstruction weight; generating image-positional line data by filtering said projection line data; determining back-projected pixel data of each pixel on the reconstruction field based on said image-positional line data; and determining backprojected data by adding the backprojected pixel data on a pixel-by-pixel basis for all views used in image reconstruction.

According to the X-ray CT imaging method in the tenth aspect, since the three-dimensional image reconstruction technique is performed as proposed in Japanese Patent Application Laid Open Nos. 2002-147231 and 2002-338947, the volume of calculation can be significantly reduced.

In its eleventh aspect, the present invention provides an X-ray CT apparatus characterized in comprising: an X-ray tube; a multi-row detector; helical scanning means for collecting projection data while making relative rotation of at least one of said X-ray tube and said multi-row detector around a subject to be imaged and making relative rectilinear motion of them with respect to the subject to be imaged, from a rectilinear motion start point to a rectilinear motion end point defined within a region of interest (ROI) for which a CT image is to be created; and image reconstructing means for producing a CT image at a desired image position in said region of interest using the collected projection data.

According to the X-ray CT apparatus in the eleventh aspect, the X-ray CT imaging method in the first aspect is suitably implemented.

In its twelfth aspect, the present invention provides the X-ray CT apparatus having the aforementioned configuration, characterized in that: said rectilinear motion start point lies inward from the ROI front end position by half or approximately half of the X-ray beam thickness in the direction of rectilinear motion.

According to the X-ray CT apparatus in the twelfth aspect, the X-ray CT imaging method in the second aspect is suitably implemented.

In its thirteenth aspect, the present invention provides the X-ray CT apparatus having the aforementioned configuration, characterized in that: said rectilinear motion end point lies inward from the ROI back end position by half or about half of the X-ray beam thickness in the direction of rectilinear motion.

According to the X-ray CT apparatus in the thirteenth aspect, the X-ray CT imaging method in the third aspect is suitably implemented.

In its fourteenth aspect, the present invention provides an X-ray CT apparatus characterized in comprising: an X-ray tube; a multi-row detector; helical scanning means for collecting projection data from a rectilinear motion start point to a rectilinear motion end point while making relative rotation of at least one of said X-ray tube and said multi-row detector around a subject to be imaged and making relative rectilinear motion of them with respect to the subject to be imaged; and image reconstructing means for creating a CT image at a desired image position in a region of interest (ROI) from an ROI front end position anterior to said rectilinear motion start point to an ROI back end position posterior to said rectilinear motion end point using the collected projection data.

According to the X-ray CT apparatus in the fourteenth aspect, the X-ray CT imaging method in the fourth aspect is suitably implemented.

In its fifteenth aspect, the present invention provides the X-ray CT apparatus having the aforementioned configuration, characterized in that: said ROI front end position lies anterior to said rectilinear motion start point by half or approximately half of the X-ray beam thickness in the direction of rectilinear motion.

According to the X-ray CT apparatus in the fifteenth aspect, the X-ray CT imaging method in the fifth aspect is suitably implemented.

In its sixteenth aspect, the present invention provides the X-ray CT apparatus having the aforementioned configuration, characterized in that: said ROI back end position lies posterior to said rectilinear motion end point by half or approximately half of the X-ray beam thickness in the direction of rectilinear motion.

According to the X-ray CT apparatus in the sixteenth aspect, the X-ray CT imaging method in the sixth aspect is suitably implemented.

In its seventeenth aspect, the present invention provides the X-ray CT apparatus having the aforementioned configuration, characterized in that said helical scanning means collects the projection data while making reciprocal relative rectilinear motion by: making motion from said rectilinear motion start point to said rectilinear motion end point; then re-defining said rectilinear motion start point and said rectilinear motion end point as a new rectilinear motion end point and a new rectilinear motion start point, respectively; and making relative rectilinear motion in an opposite direction.

According to the X-ray CT apparatus in the seventeenth aspect, the X-ray CT imaging method in the seventh aspect is suitably implemented.

In its eighteenth aspect, the present invention provides the X-ray CT apparatus having the aforementioned configuration, characterized in that: said helical scanning means collects projection data while making said relative rotation at said rectilinear motion start point without making said relative rectilinear motion; reconstructs a CT image using the collected projection data; and starts said relative rectilinear motion based on a change in said CT image.

According to the X-ray CT apparatus in the eighteenth aspect, the X-ray CT imaging method in the eighth aspect is suitably implemented.

In its nineteenth aspect, the present invention provides the X-ray CT apparatus having the aforementioned configuration, characterized in that: said image reconstructing means creates a CT image by a three-dimensional image reconstruction technique.

According to the X-ray CT apparatus in the nineteenth aspect, the X-ray CT imaging method in the ninth aspect is suitably implemented.

In its twentieth aspect, the present invention provides the X-ray CT apparatus having the aforementioned configuration, characterized in that: said three-dimensional image reconstruction technique is a three-dimensional backprojection method comprising: ordering the collected projection data based on the z-position of each view and extracting projection data corresponding to one line or a plurality of parallel lines at spacings of a plurality of pixels on an image reconstruction field; generating projection line data by multiplying said projection data by a cone beam reconstruction weight; generating image-positional line data by filtering said projection line data; determining backprojected pixel data of each pixel on the reconstruction field based on said image-positional line data; and determining backprojected data by adding the backprojected pixel data on a pixel-by-pixel basis for all views used in image reconstruction.

According to the X-ray CT apparatus in the twentieth aspect, the X-ray CT imaging method in the tenth aspect is suitably implemented.

According to the X-ray CT imaging method and X-ray CT apparatus of the present invention, the distance of rectilinear motion in a helical scan can be reduced. Thus, the cycle time for reciprocal rectilinear motion can be reduced. Moreover, the X-ray exposure dose can be reduced even if X-rays are constantly emitted during rectilinear motion.

The X-ray CT imaging method and X-ray CT apparatus of the present invention can be employed in, for example, perfusion CT.

Further objects and advantages of the present invention will be apparent from the following description of the preferred embodiments of the invention as illustrated in the accompanying drawings.

BRIEF DESCRIPTION OF THE DRAWINGS

FIG. 4 is a flow chart showing the general operation of the X-ray CT apparatus of Example 1.

FIG. 5 is an explanatory diagram showing a data structure.

DETAILED DESCRIPTION OF THE INVENTION

The present invention will now be described in more detail with reference to embodiments shown in the accompanying drawings. It should be noted that the present invention is not limited to the embodiments.

EXAMPLE 1

Figure 1:
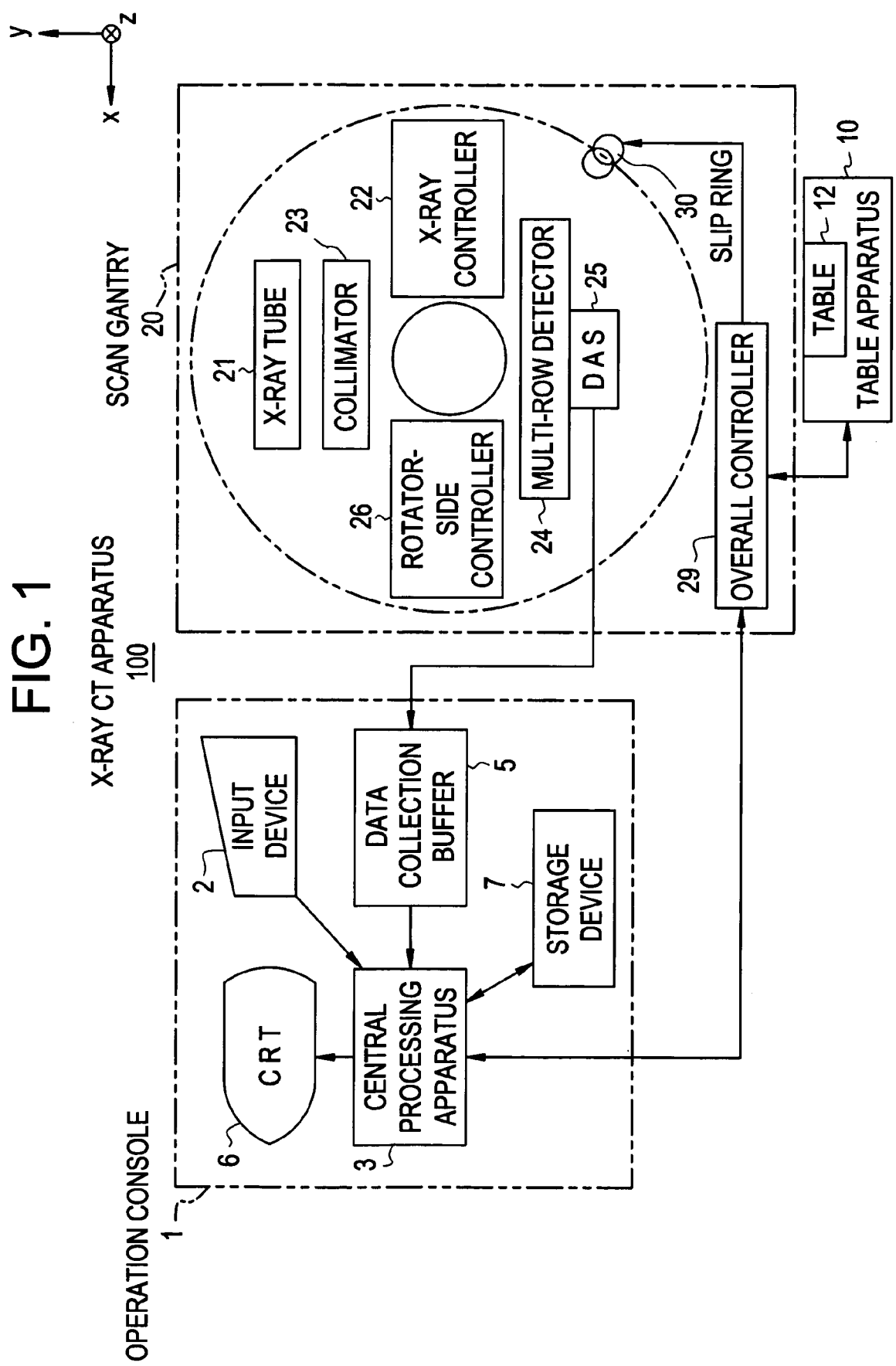
FIG. 1 is a block diagram showing the configuration of an X-ray CT apparatus of Example 1.

FIG. 1 is a block diagram showing the configuration of an X-ray CT apparatus 100 of Example 1.

The X-ray CT apparatus 100 comprises an operation console 1, a table apparatus 10, and a scan gantry 20.

The operation console 1 comprises an input device 2 for accepting inputs by a human operator, a central processing apparatus 3 for executing image reconstruction processing etc., a data collection buffer 5 for collecting projection data acquired at the scan gantry 20, a CRT 6 for displaying a CT image reconstructed from the projection data, and a storage device 7 for storing programs, data, and X-ray CT images.

The table apparatus 10 comprises a table 12 for laying thereon a subject and transporting the subject into/out of a bore (cavity portion) of the scan gantry 20. The table 12 is vertically and horizontally/rectilinearly moved by a motor incorporated in the table apparatus 10.

The scan gantry 20 comprises an X-ray tube 21, an X-ray controller 22, a collimator 23, a multi-row detector 24, a DAS (data acquisition system) 25, a rotator-side controller 26 for controlling the X-ray controller 22, collimator 23 and DAS 25, an overall controller 29 for communicating control signals etc. with the operation console 1 and imaging table 10, and a slip ring 30.

Figure 2:
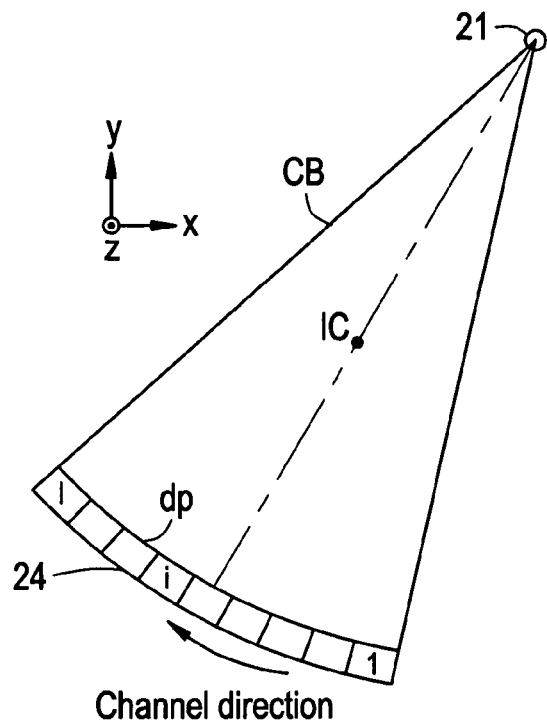
FIG. 2 is an explanatory diagram showing a rotation of an X-ray tube and a multi-row detector.
Figure 3:
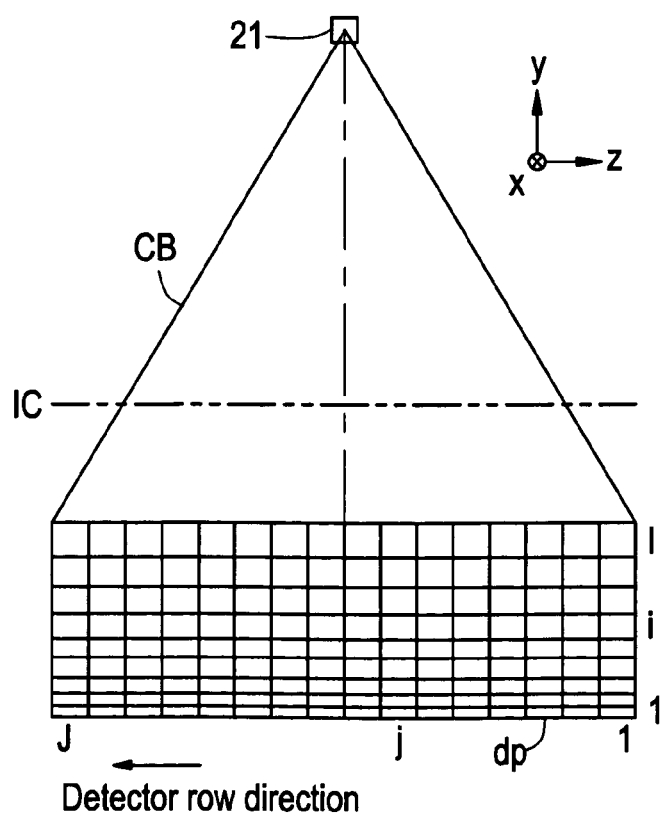
FIG. 3 is an explanatory diagram showing an X-ray beam (cone beam).

FIGS. 2 and 3 are explanatory diagrams of the X-ray tube 21 and multi-row detector 24.

The X-ray tube 21 and multi-row detector 24 rotate around an isocenter IC. Representing the direction of rectilinear motion of the table 12 as a z-direction, a direction perpendicular to the upper surface of the table 12 as a y-direction, and a direction orthogonal to the z- and y-directions as an x-direction, a plane of rotation of the X-ray tube 21 and multi-row detector 24 is an x-y plane.

The X-ray tube 21 generates an X-ray beam generally referred to as a cone beam CB. When the direction of the center axis of the cone beam CB is parallel to the y-direction, view=0° is defined.

The multi-row detector 24 has J (e.g., J=256) detector rows. Each row has I (e.g., I=1,024) channels.

FIG. 4 is a flow chart showing the general operation of the X-ray CT apparatus 100.

At Step S1, projection data D0(z, view, j, i) represented by the rectilinear motion position z, view angle view, detector row index j and channel index i is collected while rotating the X-ray tube 21 and multi-row detector 24 around the subject to be imaged and rectilinearly moving the table 12. The rectilinear motion position z is obtained by an encoder counting a z-position pulse, converted into a z-coordinate at the overall controller 29, passed via the slip ring 30, and appended as z-coordinate information to the projection data from the DAS 25.

FIG. 5 shows a format of the projection data at a certain view appended with the z-coordinate information.

The data collection processing at Step S1 will be discussed later with reference to FIG. 6.

At Step S2, the projection data D0(z, view, j, i) is subjected to pre-processing (offset correction, log correction, X-ray dose correction and sensitivity correction).

At Step S3, the pre-processed projection data D0(z, view, j, i) is filtered. Specifically, the data is subjected to Fourier transformation, multiplied by a filter (reconstruction function), and then subjected to inverse Fourier transformation.

At Step S4, the filtered projection data D0(z, view, j, i) is subjected to three-dimensional backprojection processing to determine backprojected data D3(x, y).

The three-dimensional backprojection processing at Step S4 will be discussed later with reference to FIG. 8.

At Step S5, the backprojected data D3(x, y) is subjected to post-processing to obtain a CT image.

Figure 6:
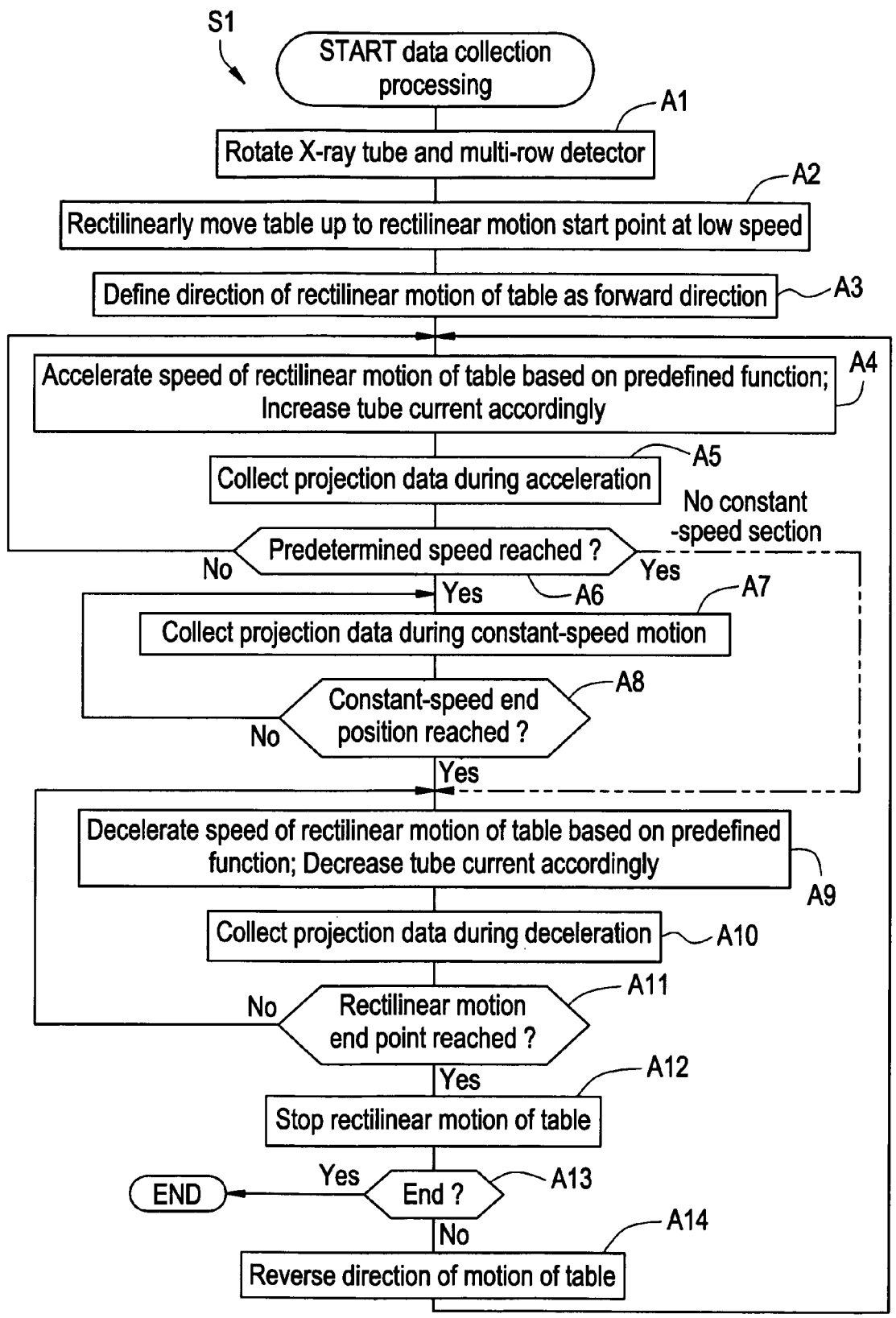
FIG. 6 is a flow chart showing details of data collection processing of Example 1.

FIG. 6 is a flow chart showing details of the data collection processing (Step S1 in FIG. 4).

At Step A1, the X-ray tube 21 and multi-row detector 24 are rotated around the subject to be imaged.

Figure 7:
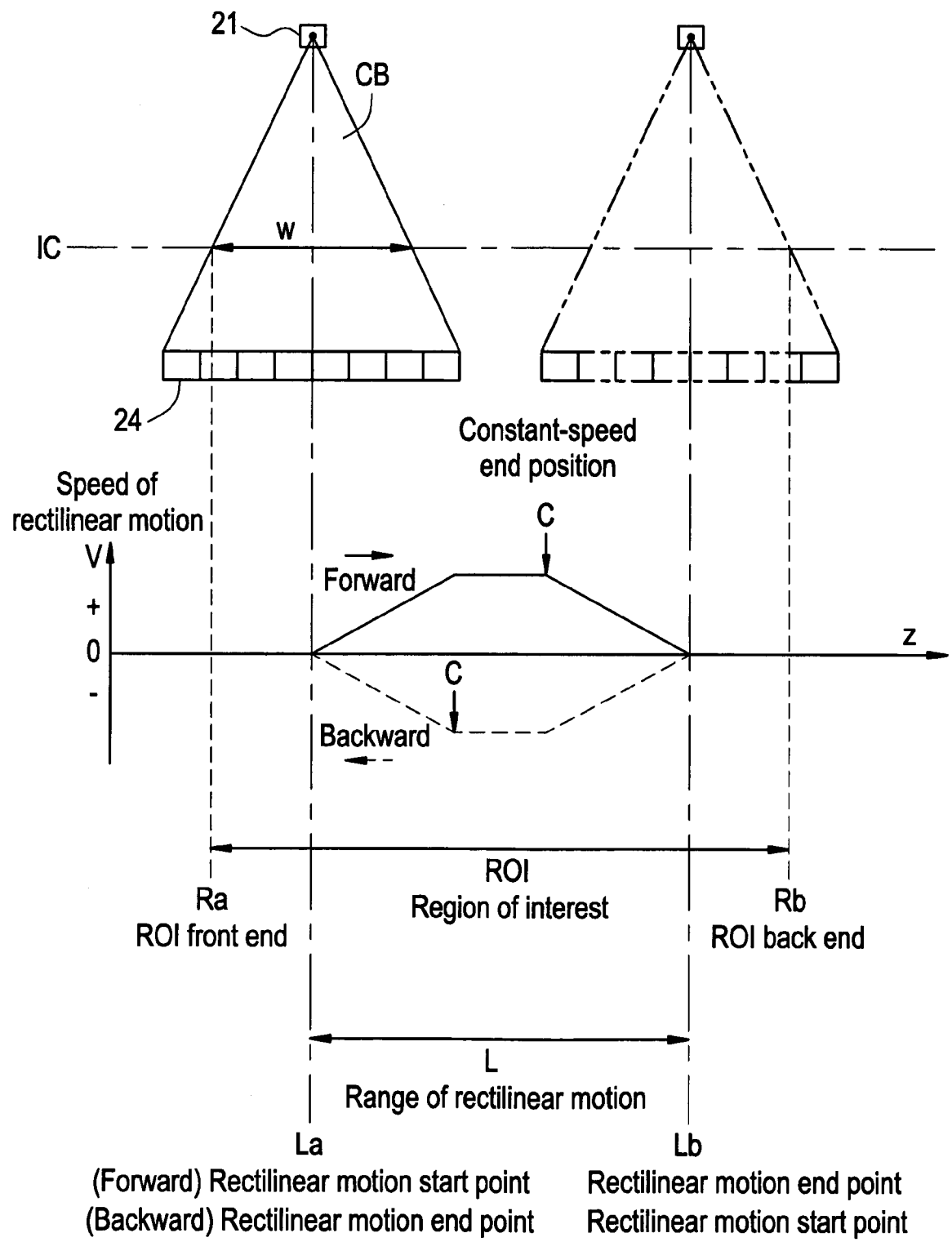
FIG. 7 is an explanatory diagram showing a region of interest and a range of rectilinear motion of Example 1.

At Step A2, the table 12 is rectilinearly moved at a low speed up to a rectilinear motion start point La shown in FIG. 7. The rectilinear motion start point La is defined inward from the ROI front end Ra by half or approximately half of the X-ray beam thickness w in the direction of rectilinear motion at the center of rotation IC.

At Step A3, the direction of rectilinear motion of the table 12 is defined as a forward direction (+z-direction here).

At Step A4, the speed of rectilinear motion of the table 12 is accelerated based on a predefined function. Moreover, the tube current is increased accordingly. The predefined function may be linear or non-linear versus time. Since the X-ray density in the direction of rectilinear motion, i.e., the amount of X-rays per unit thickness, is proportional to the ratio "tube current/speed of rectilinear motion," the tube current is increased with the increase in the speed of rectilinear motion to make the ratio "tube current/speed of rectilinear motion" constant. Thus, the X-ray density in the direction of rectilinear motion can be made constant even during acceleration.

At Step A5, projection data D0(z, view, j, i) during acceleration are collected.

At Step A6, when the speed of rectilinear motion of the table 12 reaches a predetermined speed, the process goes to Step A7; otherwise, goes back to Step A4 to further accelerate the table 12. The predetermined speed is a maximum desired motion speed of the table 12.

At Step A7, projection data D0(z, view, j, i) during constant-speed motion are collected while keeping the speed of rectilinear motion of the table 12 at the predetermined speed.

At Step A8, if the table 12 reaches a constant-speed end position C shown in FIG. 7, the process goes to Step A9; otherwise, goes back to Step A7 to continue the projection data collection during constant-speed motion.

At Step A9, the speed of rectilinear motion of the table 12 is decelerated based on a predefined function. Moreover, the tube current is decreased accordingly. The predefined function may be linear or non-linear versus time. Since the X-ray density in the direction of rectilinear motion, i.e., the amount of X-rays per unit thickness, is proportional to the ratio "tube current/speed of rectilinear motion," the tube current is decreased with the decrease in the speed of rectilinear motion to make the ratio "tube current/speed of rectilinear motion" constant. Thus, the X-ray density in the direction of rectilinear motion can be made constant even during deceleration.

At Step A10, projection data D0(z, view, j, i) during deceleration are collected.

At Step A11, if the table 12 reaches a rectilinear motion end point Lb shown in FIG. 7, the process goes to Step A12; otherwise, goes back to Step A9 to deceleratingly move the table 12. The rectilinear motion end point Lb is defined inward from the ROI back end Rb by half or approximately half of the X-ray beam thickness w in the direction of rectilinear motion at the center of rotation IC.

At Step A12, rectilinear motion of the table 12 is stopped.

At Step A13, if intended data collection is completed, the process is terminated; otherwise goes to Step A14.

At Step A14, the direction of movement of the table 12 is re-defined as the opposite direction. The process then goes back to Step A4 to continue data collection. Specifically, the previous rectilinear motion end point Lb is defined as a current rectilinear motion start point, the previous rectilinear motion start point La is defined as a current rectilinear motion end point, and projection data are collected while rectilinearly moving the table 12 in the 19. direction opposite to the previous direction.

As can be seen from FIG. 7, when the multi-row detector 24 is employed, the X-ray beam CB covers as far as the ROI front end Ra even if the rectilinear motion start point La is defined within the region of interest ROI, because the X-ray beam thickness w in the direction of rectilinear motion is large. Similarly, the X-ray beam CB covers as far as the ROI back end Rb even if the rectilinear motion end point Lb is defined within the region of interest ROI. Therefore, a CT image can be created at a desired image position from the ROI front end Ra to the ROI back end Rb using the collected projection data.

It should be noted that if the region of interest ROI is short, the constant-speed section may be absent. In such a case, Steps A7 and A8 are skipped.

Figure 8:
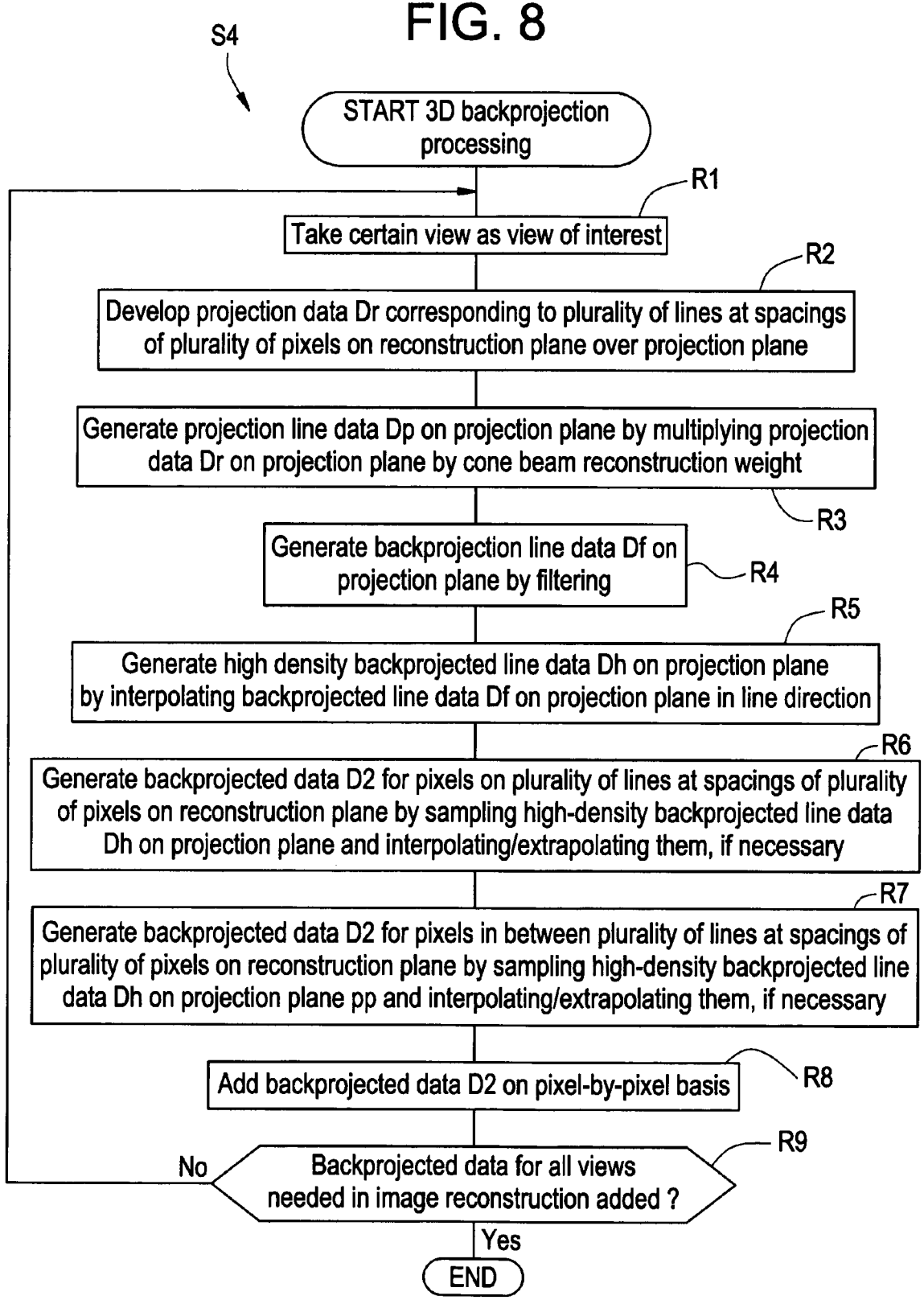
FIG. 8 is a flow chart showing details of three-dimensional image reconstruction processing.

FIG. 8 is a flow chart showing details of the three-dimensional backprojection processing (Step S4 in FIG. 4).

At Step R1, one view is taken as a view of interest from among all views needed for reconstruction of a CT image for a reconstruction plane P at a desired image position.

At Step R2, projection data Dr corresponding to a plurality of parallel lines at spacings of a plurality of pixels on the reconstruction plane P are extracted from among the projection data D0(z, view, j, i) at the view of interest.

Figure 9A:
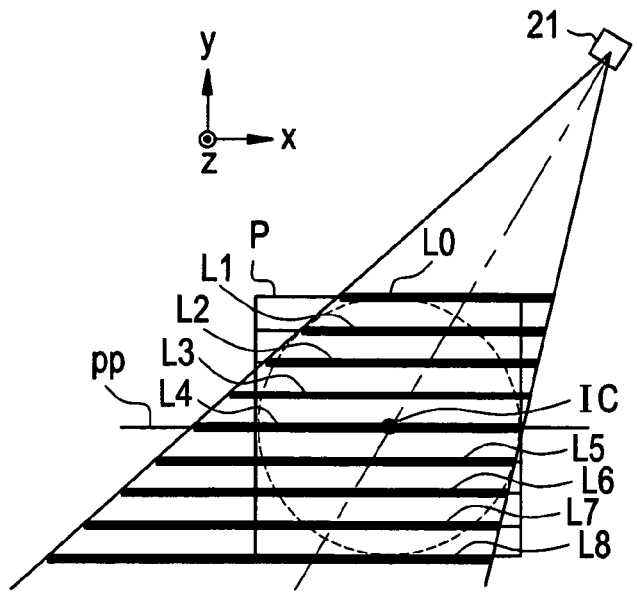
FIG. 9 is a conceptual diagram showing lines on a reconstruction plane P projected in the direction of X-ray transmission.
Figure 9B:
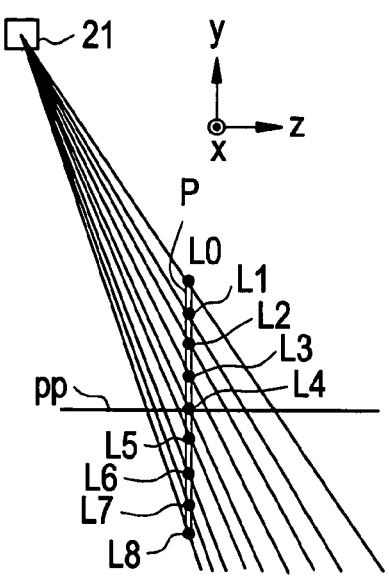

FIGS. 9a and FIG. 9b show a plurality of parallel lines L0–L8 on the reconstruction plane P.

The number of lines is $\frac{1}{64}$–$\frac{1}{2}$ of the maximum number of pixels in the reconstruction plane in a direction orthogonal to the lines. For example, if the number of pixels in the reconstruction plane P is 512×512, the number of lines is nine.

Moreover, the line direction is defined as the x-direction for $-45° \leq view < 45°$ (or a view angle range mainly including the range and also including its vicinity) and $135° \leq view < 225°$ (or a view angle range mainly including the range and also including its vicinity). The line direction is defined as the y-direction for $45° \leq view < 135°$ (or a view angle range mainly including the range and also including its vicinity) and $225° \leq view < 315°$ (or a view angle range mainly including the range and also including its vicinity).

Furthermore, a projection plane pp is assumed to pass through the center of rotation IC and be parallel to the lines L0–L8.

Figure 10:
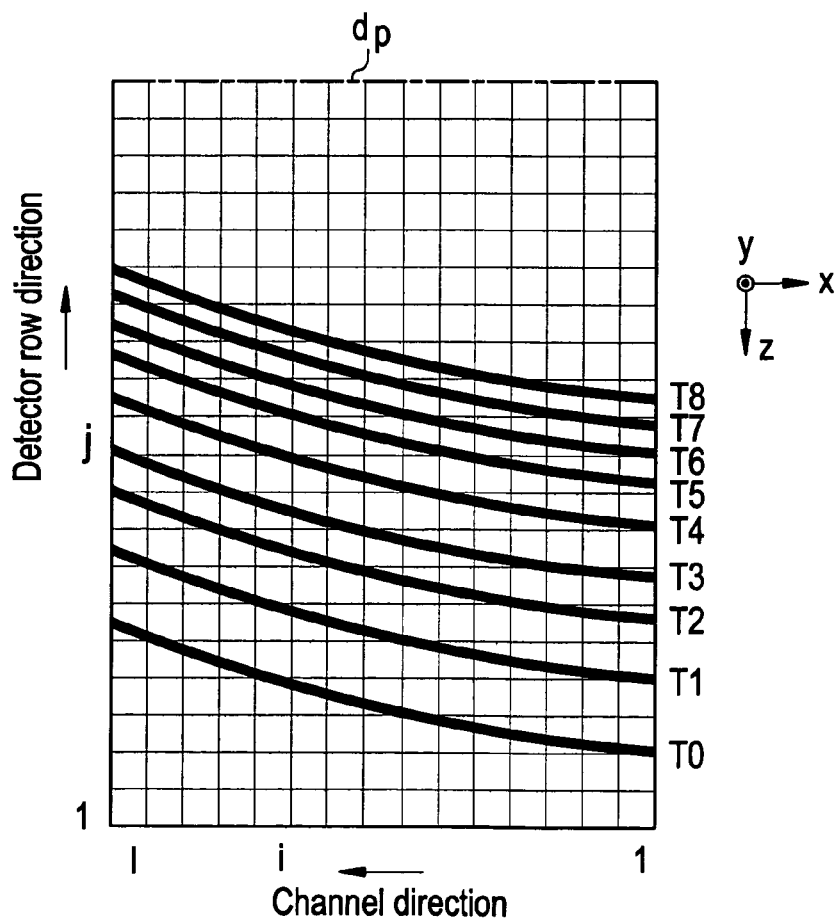
FIG. 10 is a conceptual diagram showing lines on the reconstruction plane P projected onto a detector plane.

FIG. 10 shows lines T0–T8 formed by projecting the plurality of parallel lines L0–L8 on the reconstruction plane P onto a detector plane dp in a direction of X-ray transmission.

The direction of X-ray transmission is determined depending upon the geometry of the X-ray tube 21, multi-row detector 24 and lines L0–L8; since the position z of the projection data D0(z, view, j, i) in the direction of rectilinear motion is known, the direction of X-ray transmission can be accurately determined even for the projection data D0(z, view, j, i) during acceleration/deceleration.

The projection data Dr corresponding to the lines L0–L8 can be obtained by extracting projection data at the detector row j and channel i corresponding to the lines T0–T8 projected onto the detector plane dp.

Figure 11:
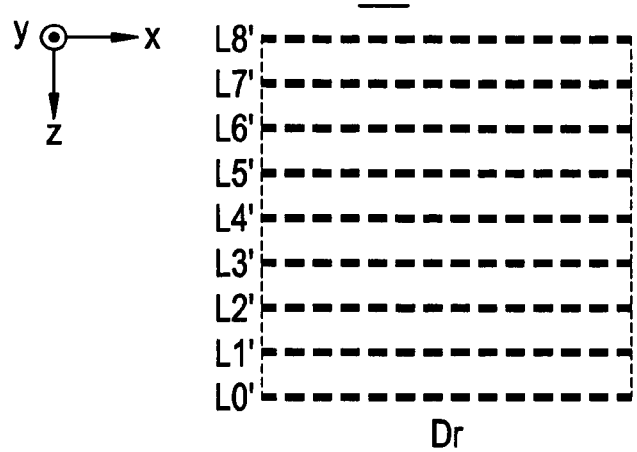
FIG. 11 is a conceptual diagram showing projection data Dr on lines on the detector plane at a view angle view=0° projected onto a projection plane.

Now lines L0'–L8' formed by projecting the lines T0–T8 onto the projection plane pp in the direction of X-ray transmission are assumed as shown in FIG. 11, and the projection data Dr are developed over the lines L0'–L8' on the projection plane pp.

Figure 12:
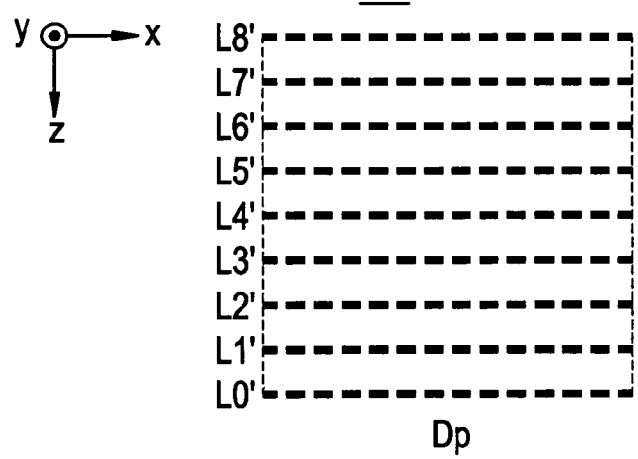
FIG. 12 is a conceptual diagram showing projection line data Dp obtained by multiplying the projection data Dr on the projection plane pp at the view angle view=0° by a cone beam reconstruction weight.

Referring again to FIG. 8, at Step R3, the projection data Dr of the lines L0'–L8' on the projection plane pp are multiplied by a cone beam reconstruction weight to generate projection line data Dp on the projection plane pp as shown in FIG. 12.

The cone beam reconstruction weight is $(r1/r0)^2$, where r0 is the distance from the focal spot of the X-ray tube 21 to the j-th detector row and the i-th channel of the multi-row detector 24 corresponding to projection data Dr, and r1 is the distance from the focal spot of the X-ray tube 21 to a point on the reconstruction plane P corresponding to the projection data Dr.

Figure 13:
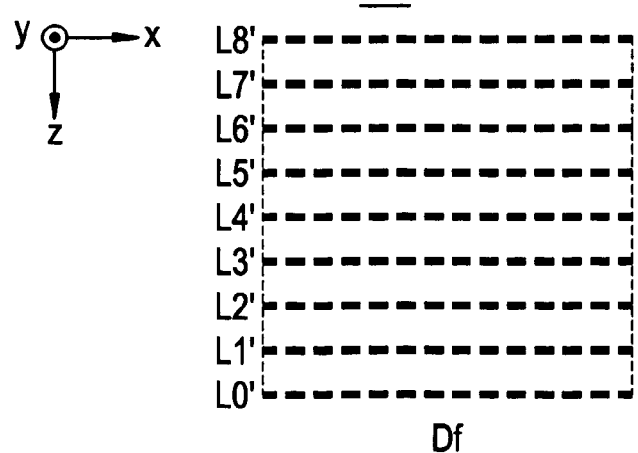
FIG. 13 is a conceptual diagram showing backprojected line data Df obtained by filtering the projection line data Dp on the projection plane pp at the view angle view=0°.

At Step R4, the projection line data Dp on the projection plane pp are filtered. Specifically, the projection line data Dp on the projection plane pp are subjected to FFT, multiplied by a filter function (reconstruction function), and subjected to inverse FFT to generate image backprojected line data Df on the projection plane pp as shown in FIG. 13.

Figure 14:
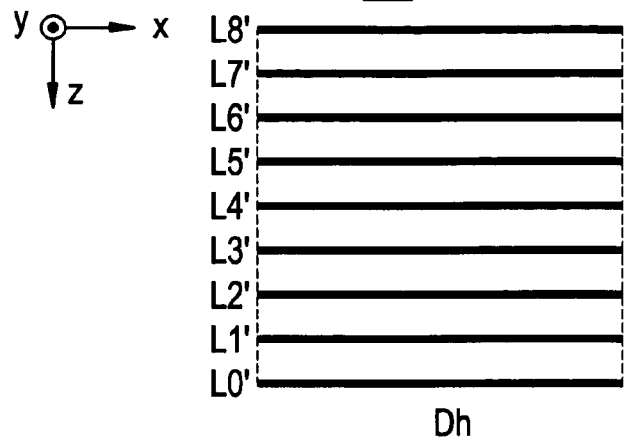
FIG. 14 is a conceptual diagram showing high density backprojected line data Dh obtained by interpolating the backprojected line data Df on the projection plane pp at the view angle view=0°.

At Step R5, the backprojected line data Df on the projection plane pp is interpolated in the line direction to generate high-density backprojected line data Dh on the projection plane pp as shown in FIG. 14.

The data density of the high-density backprojected line data Dh on the projection plane pp is 8–32 times the maximum number of pixels in the reconstruction plane P in the line direction. For example, if the factor is 16 and the number of pixels in the reconstruction plane P is 512×512, the data density is 8,192 points/line.

Figure 15:
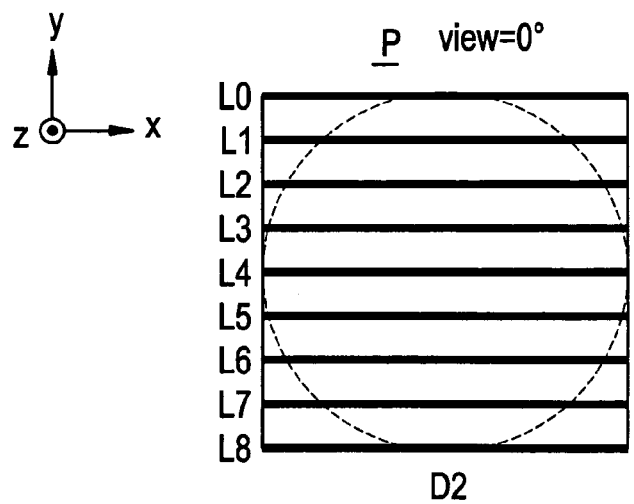
FIG. 15 is a conceptual diagram showing backprojected pixel data D2 obtained by developing the high density backprojected line data Dh on the projection plane pp at the view angle view=0° over lines on a reconstruction plane.

At Step R6, the high-density backprojected line data Dh on the projection plane pp are sampled and interpolated/extrapolated, if necessary, to generate backprojected pixel data D2 for pixels on the lines L0–L8 on the reconstruction plane P, as shown in FIG. 15.

Figure 16:
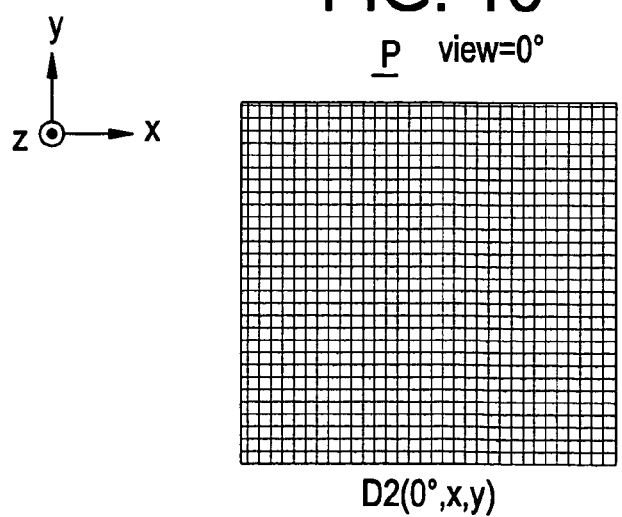
FIG. 16 is a conceptual diagram showing backprojected pixel data D2 obtained by developing the high density backprojected line data Dh on the projection plane pp at the view angle view=0° in between the lines on the reconstruction plane.
Figure 17:
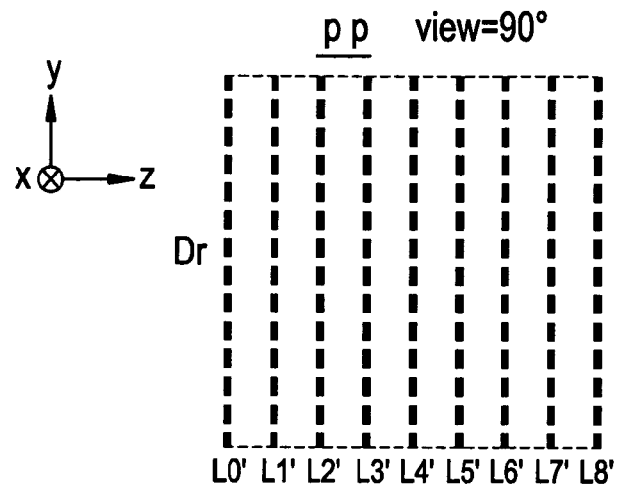
FIG. 17 is a conceptual diagram showing projection data Dr on lines on the detector plane at a view angle view=90° projected onto a projection plane.
Figure 18:
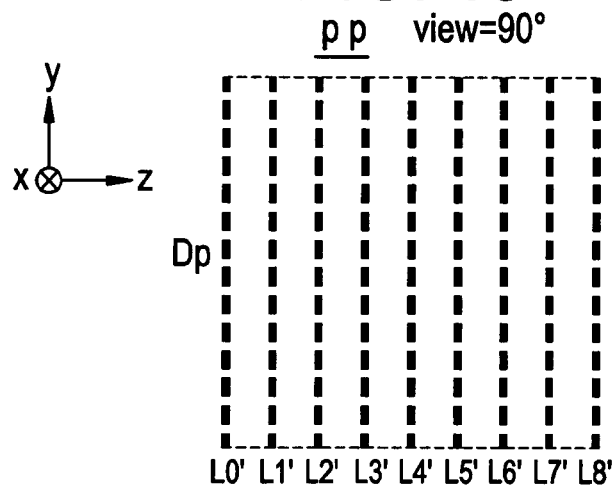
FIG. 18 is a conceptual diagram showing projection line data Dp obtained by multiplying the projection data Dr on the projection plane pp at the view angle view=90° by a cone beam reconstruction weight.
Figure 19:
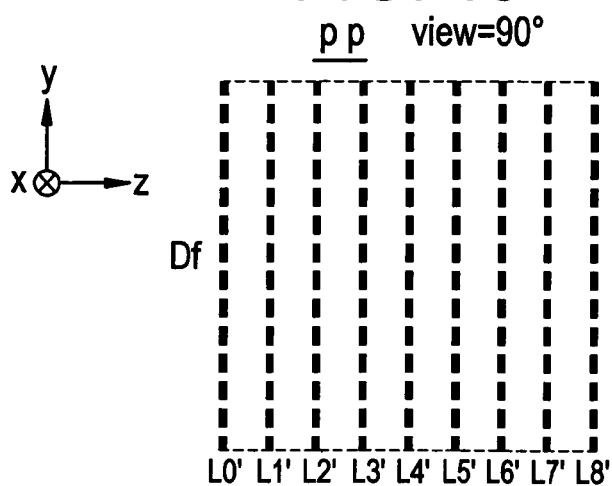
FIG. 19 is a conceptual diagram showing backprojected line data Df obtained by filtering the projection line data Dp on the projection plane pp at the view angle view=90°.
Figure 20:
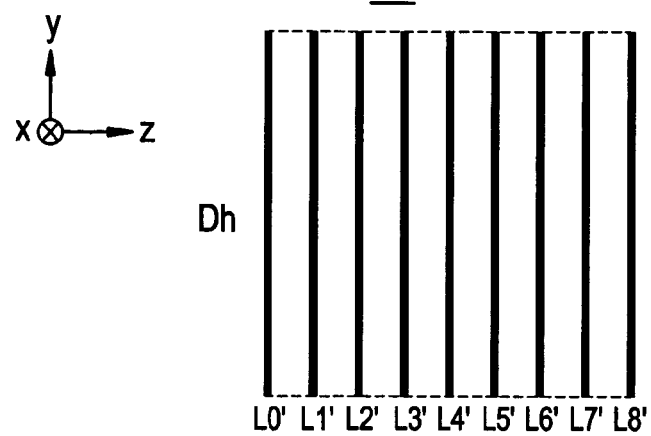
FIG. 20 is a conceptual diagram showing high density backprojected line data Dh obtained by interpolating the backprojected line data Df on the projection plane pp at the view angle view=90°.
Figure 21:
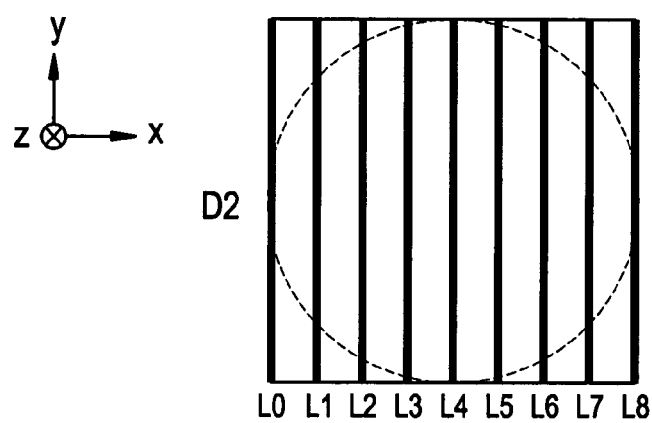
FIG. 21 is a conceptual diagram showing backprojected pixel data D2 obtained by developing the high density backprojected line data Dh on the projection plane pp at the view angle view=90° over lines on a reconstruction plane.

At Step R7, the high-density backprojected line data Dh are sampled and interpolated/extrapolated to generate back-projection data D2 for pixels in between the lines L0–L8, as shown in FIG. 16. Alternatively, the interpolation/extrapolation is conducted based on the backprojected pixel data D2 for pixels on the lines L0–L8 on the reconstruction plane P to generate backprojected pixel data D2 for pixels in between the lines L0–L8.

In FIGS. 11–16, $-45° \leq view < 45°$ (or a view angle range mainly including the range and also including its vicinity) and $135° \leq view < 225°$ (or a view angle range mainly including the range and also including its vicinity) are assumed, while FIGS. 17–22 are applied for 45°≦view<135° (or a view angle range mainly including the range and also including its vicinity) and 225°≦view<315° (or a view angle range mainly including the range and also including its vicinity).

Figure 22:
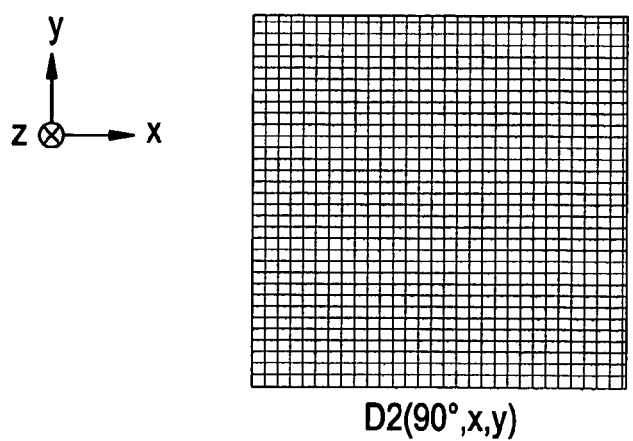
FIG. 22 is a conceptual diagram showing backprojected pixel data D2 obtained by developing the high density backprojected line data Dh on the projection plane pp at the view angle view=90° in between the lines on the reconstruction plane.
Figure 23:
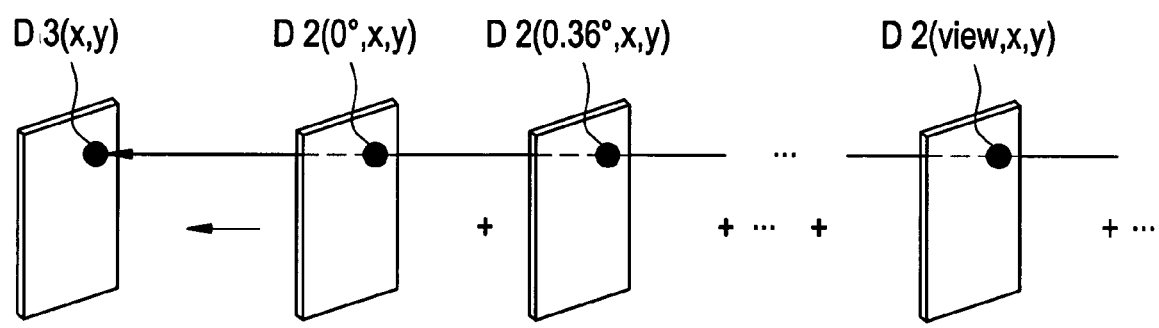
FIG. 23 is an explanatory diagram showing backprojected data D3 obtained by adding the backprojected pixel data D2 on a pixel-by-pixel basis for all views.

Referring again to FIG. 8, at Step R8, the backprojected pixel data D2 shown in FIG. 16 or 22 are added on a pixel-by-pixel basis, as shown in FIG. 23.

At Step R9, Steps R1–R8 are repeated for all views needed in reconstruction of a CT image (i.e., views for 360° or for "180°+fan angle") to obtain backprojected data D3(x, y).

Figure 24A:
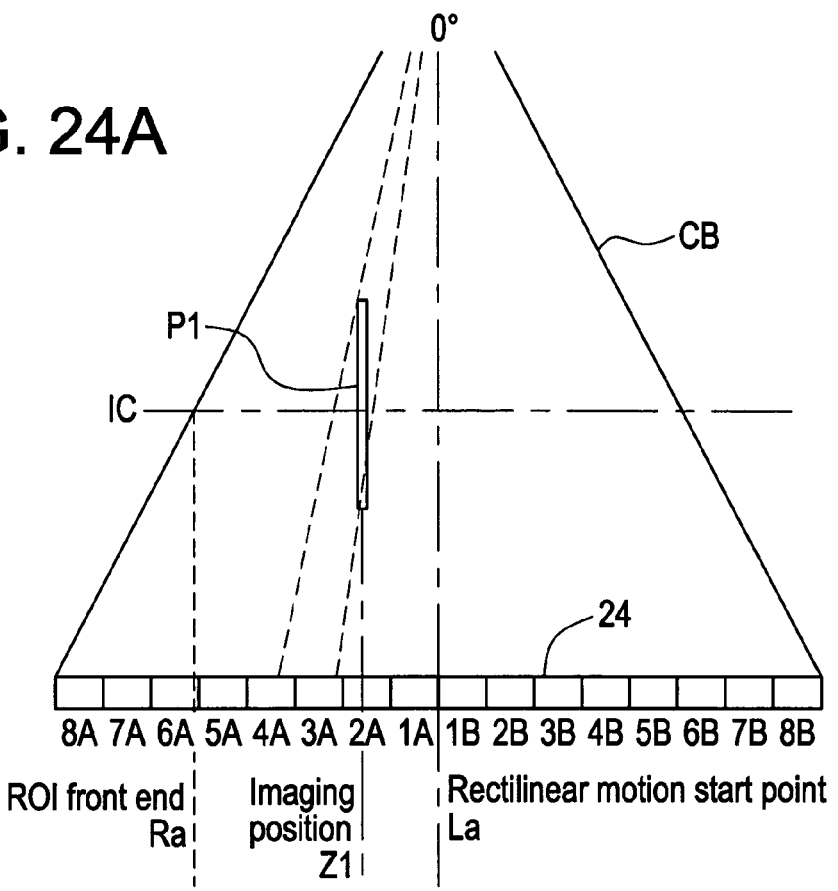
FIG. 24 is an explanatory diagram showing that a CT image can be created at an image position anterior to the rectilinear motion start point in Example 1.
Figure 24B:
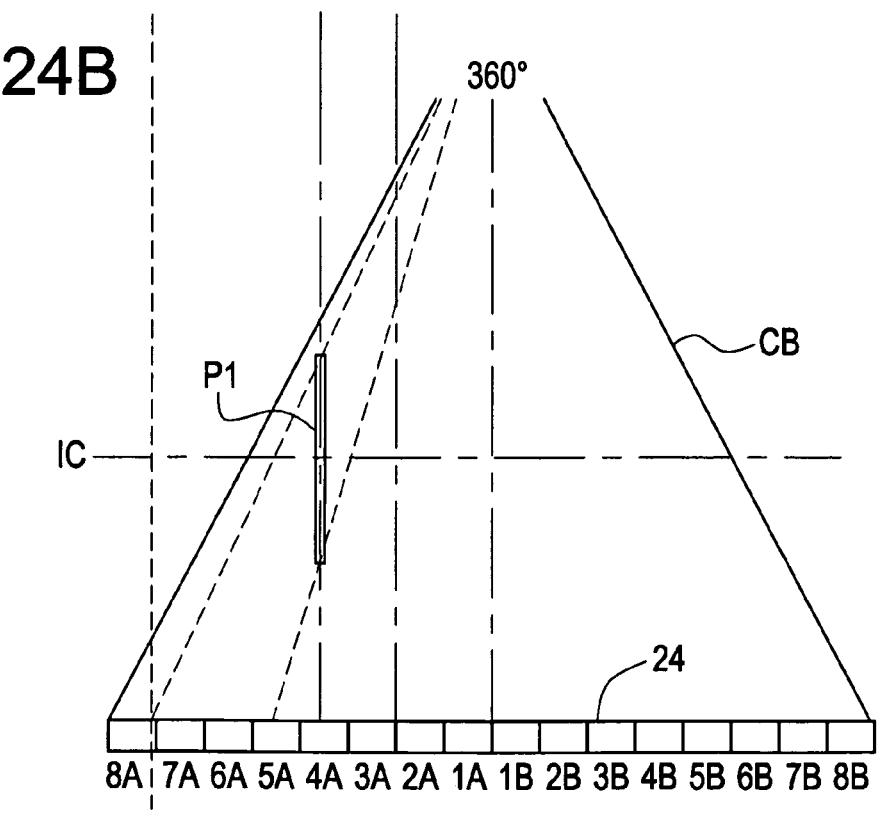

FIG. 24 is an explanatory diagram showing the relationship between a reconstruction plane P and detector rows in the multi-row detector 24.

FIG. 24(*a*) represents a view angle view=0°. At the view angle view=0°, backprojected pixel data for a reconstruction plane P1 are generated from projection data by the detector rows 3A–4A.

FIG. 24(*b*) represents a view angle view=360°. At the view angle view=360°, backprojected pixel data for the reconstruction plane P1 are generated from projection data by the detector rows 5A–7A.

Thus, backprojected data for the reconstruction plane P1 at views ranging over 360° are generated from projection data by the detector rows 3A–7A.

That is, at an image position Z1 anterior to the rectilinear motion start point La, projection data for all views needed in reconstruction of a CT image can be obtained, and therefore a CT image there can be created. Likewise, a CT image can be created at an image position posterior to the rectilinear motion end point Lb.

Figure 25A:
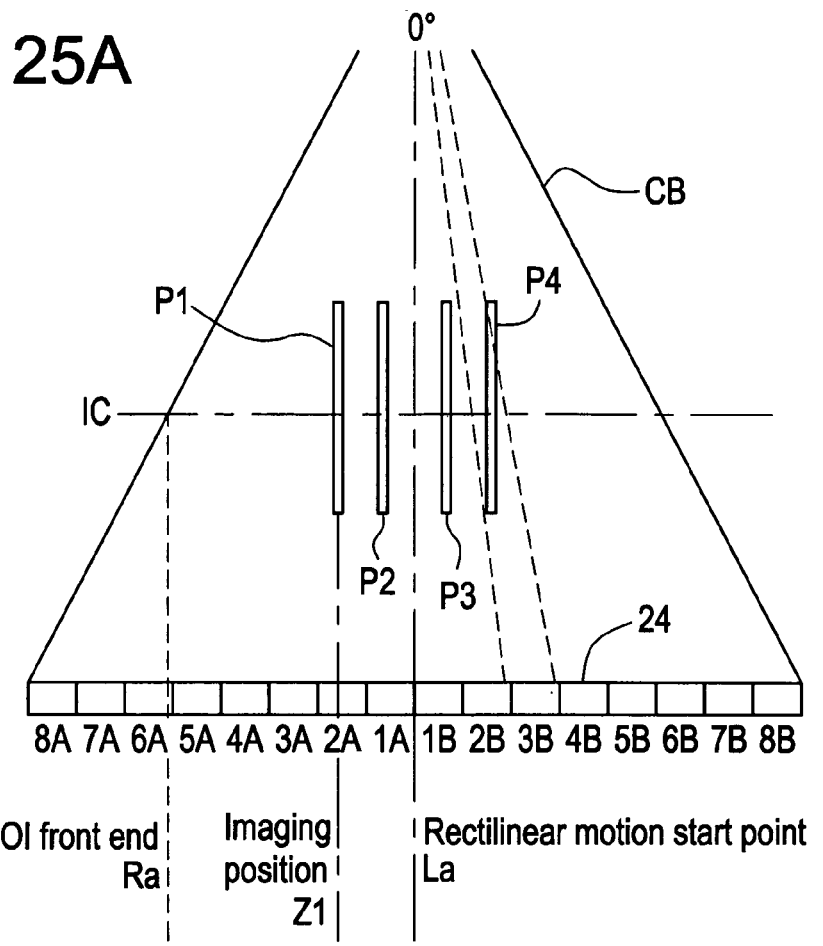
FIG. 25 is an explanatory diagram showing that a plurality of CT images can be created at a plurality of image positions, respectively, from one set of data in Example 1.
Figure 25B:
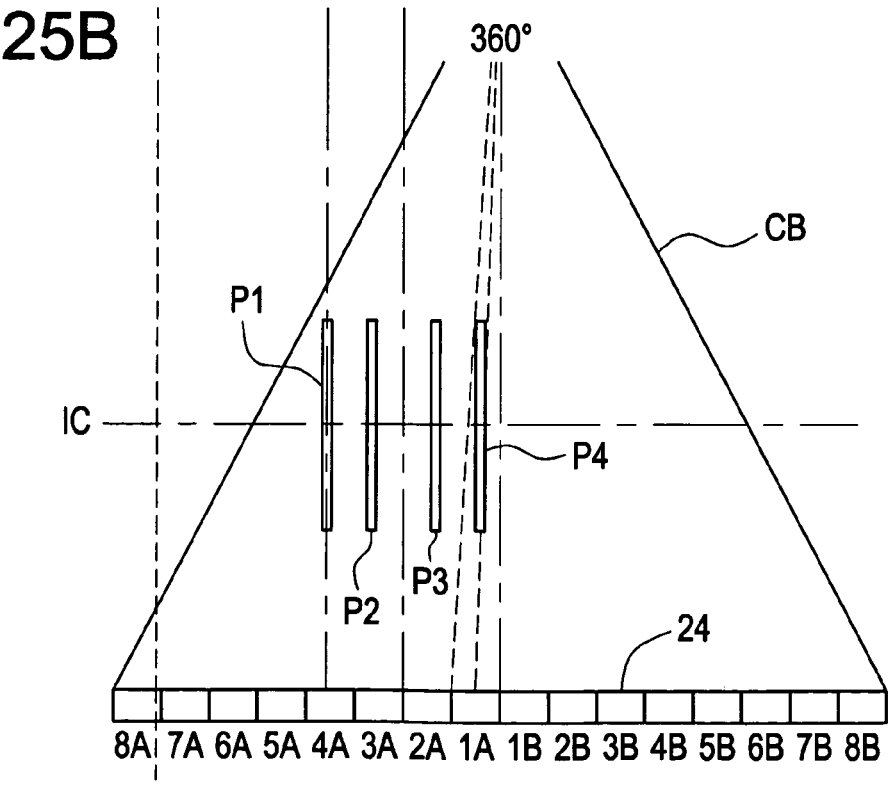

FIG. 25 is an explanatory view showing that CT images for reconstruction planes P1–P4 at a plurality of image positions can be created from projection data acquired by the multi-row detector 24 during one rotation from a view angle view=0° to a view angle view=360°.

As shown in FIG. 25(*a*), at the view angle view=0°, backprojected pixel data for the reconstruction plane P4 can be generated from projection data by the detector rows 2B–3B.

As shown in FIG. 25(*b*), at the view angle view=360°, backprojected pixel data for the reconstruction plane P4 can be generated from projection data by the detector row 1A.

Therefore, backprojected data for the reconstruction planes P1–P4 at views ranging over 360° are generated from projection data by the detector rows 3A–3B.

That is, a plurality of CT images can be created from one set of data.

According to the X-ray CT apparatus 100 of Example 1, the distance of rectilinear motion in a helical scan can be reduced. Thus, the imaging can be reduced. Moreover, the cycle time for reciprocal rectilinear motion can be reduced to improve temporal resolution at the same image position, and thus, the X-ray CT apparatus 100 of Example 1 is especially well-suited for perfusion CT. Furthermore, the X-ray exposure dose can be reduced.

EXAMPLE 2

The technique for image reconstruction may be a conventionally known three-dimensional image reconstruction technique according to the Feldkamp method. Moreover, three-dimensional image reconstruction techniques proposed in Japanese Patent Application Laid Open Nos. 2002-066420, 2002-147061, 2002-147231, 2002-235561, 2002-235662, 2002-267833, 2002-322756 and 2002-338947 may be employed.

EXAMPLE 3

The technique for image reconstruction may be a two-dimensional image reconstruction technique.

Figure 26A:
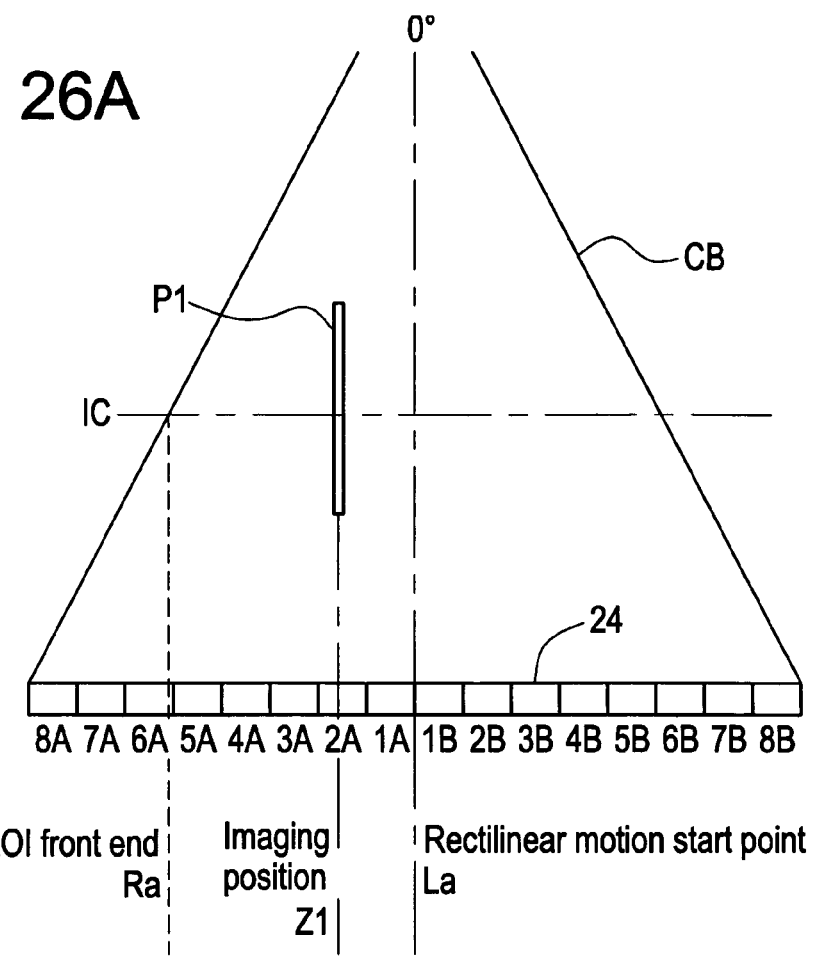
FIG. 26 is an explanatory diagram showing that a CT image can be created at an image position anterior to the rectilinear motion start point in Example 3.
Figure 26B:
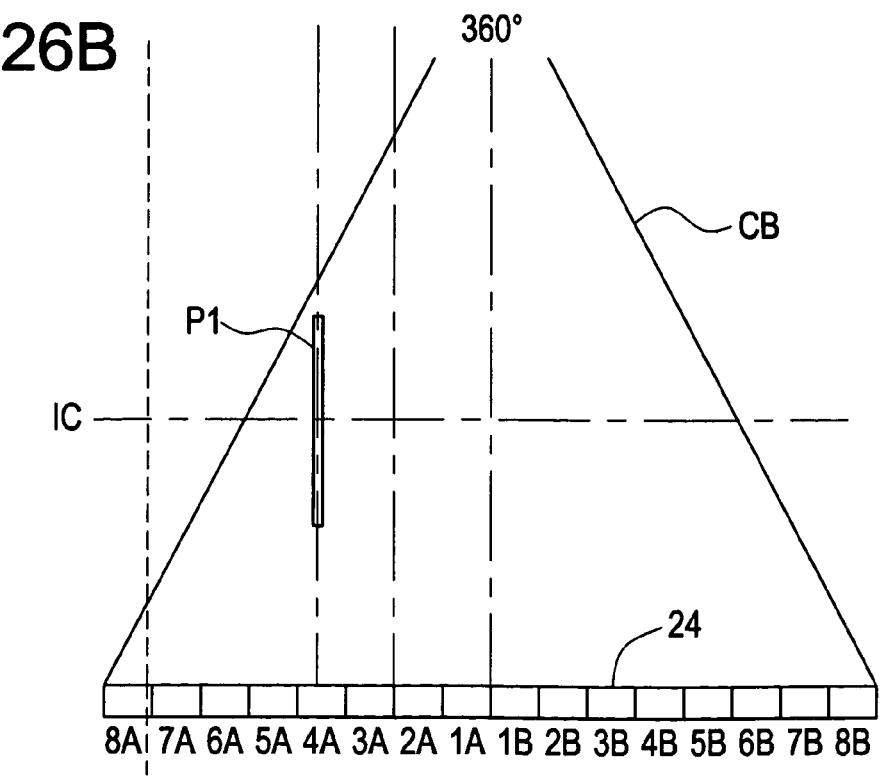

Specifically, as shown in FIG. 26(*a*), at a view angle view=0°, projection data by one detector row 2A corresponding to an image position Z1 is used. Similarly, as shown in FIG. 26(*b*), at a view angle view=360°, projection data by one detector row 4A corresponding to the image position Z1 is used. Thus, projection data for the detector rows 1A–4B are used to provide all projection data for the reconstruction plane P1 at views ranging over 360°, and then a known two-dimensional image reconstruction technique can be employed to create a CT image.

Figure 27A:
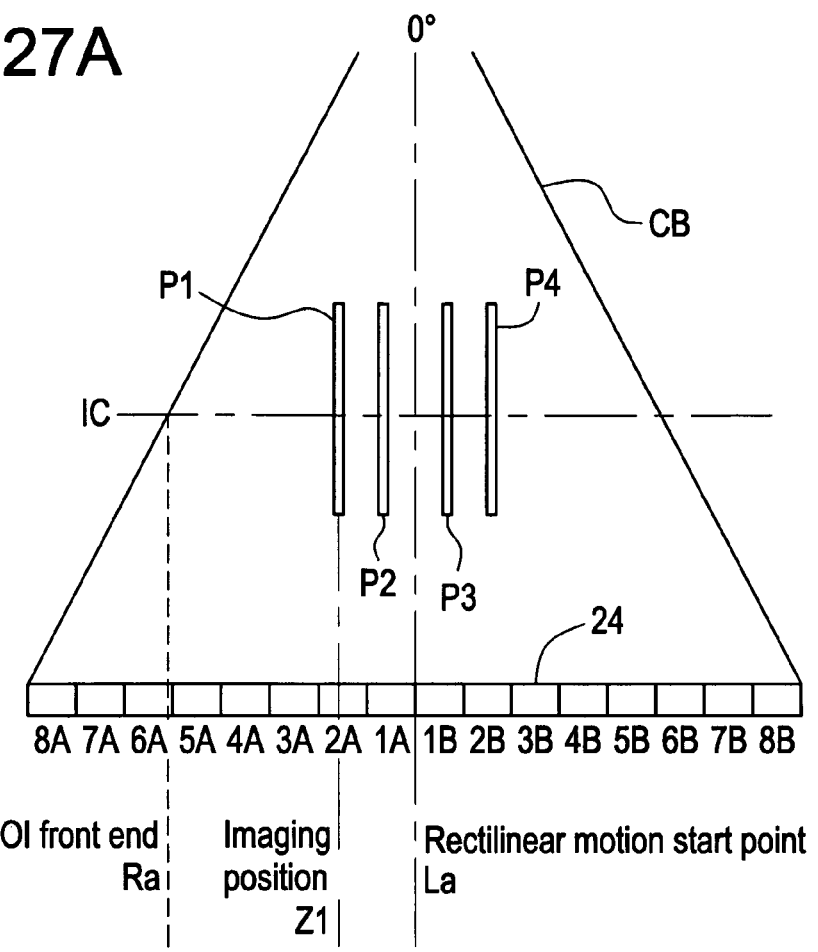
FIG. 27 is an explanatory diagram showing that a plurality of CT images can be created at a plurality of image positions, respectively, from one set of data in Example 3.
Figure 27B:
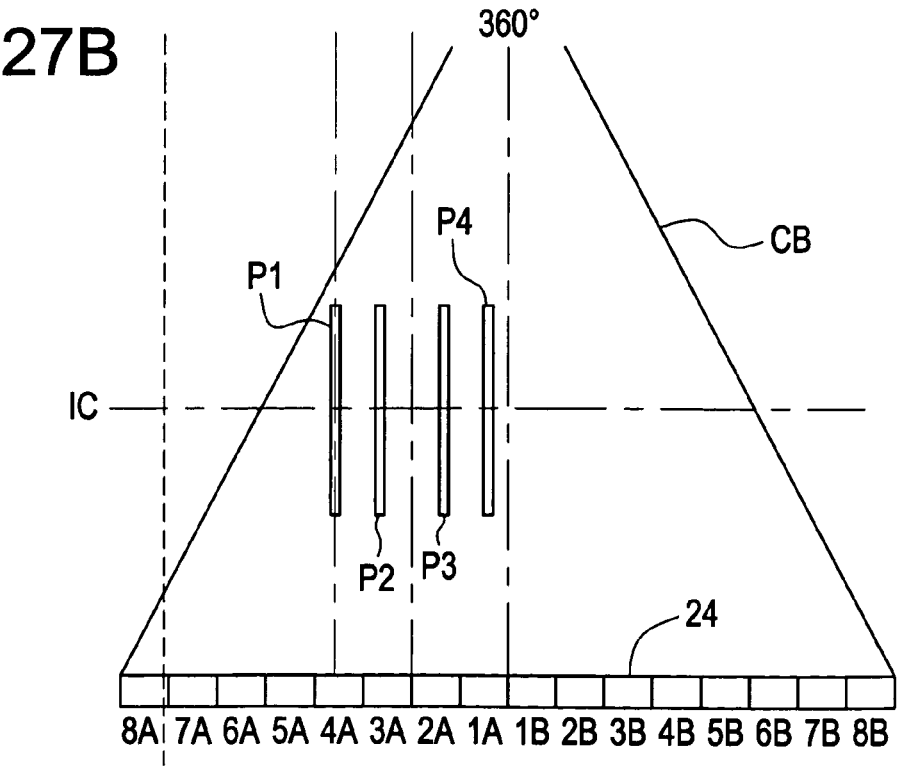

FIG. 27 is an explanatory diagram showing that CT images for reconstruction planes P1–P4 at a plurality of image positions can be created from projection data acquired by the multi-row detector 24 during one rotation from a view angle view=0° to a view angle view=360°.

As shown in FIG. 27(*a*), at a view angle view=0°, projection data by one detector row 2B is used corresponding to a reconstruction plane P4. Similarly, as shown in FIG. 27(*b*), at a view angle view=360°, projection data by one detector row 1A is used corresponding to the reconstruction plane P4. Thus, projection data for the detector rows 4A–2B are used to provide all projection data for the reconstruction planes P1–P4 at views ranging over 360°, and then a known two-dimensional image reconstruction technique can be employed to create CT images.

That is, a plurality of CT images can be created from one set of data.

EXAMPLE 4

Figure 28:
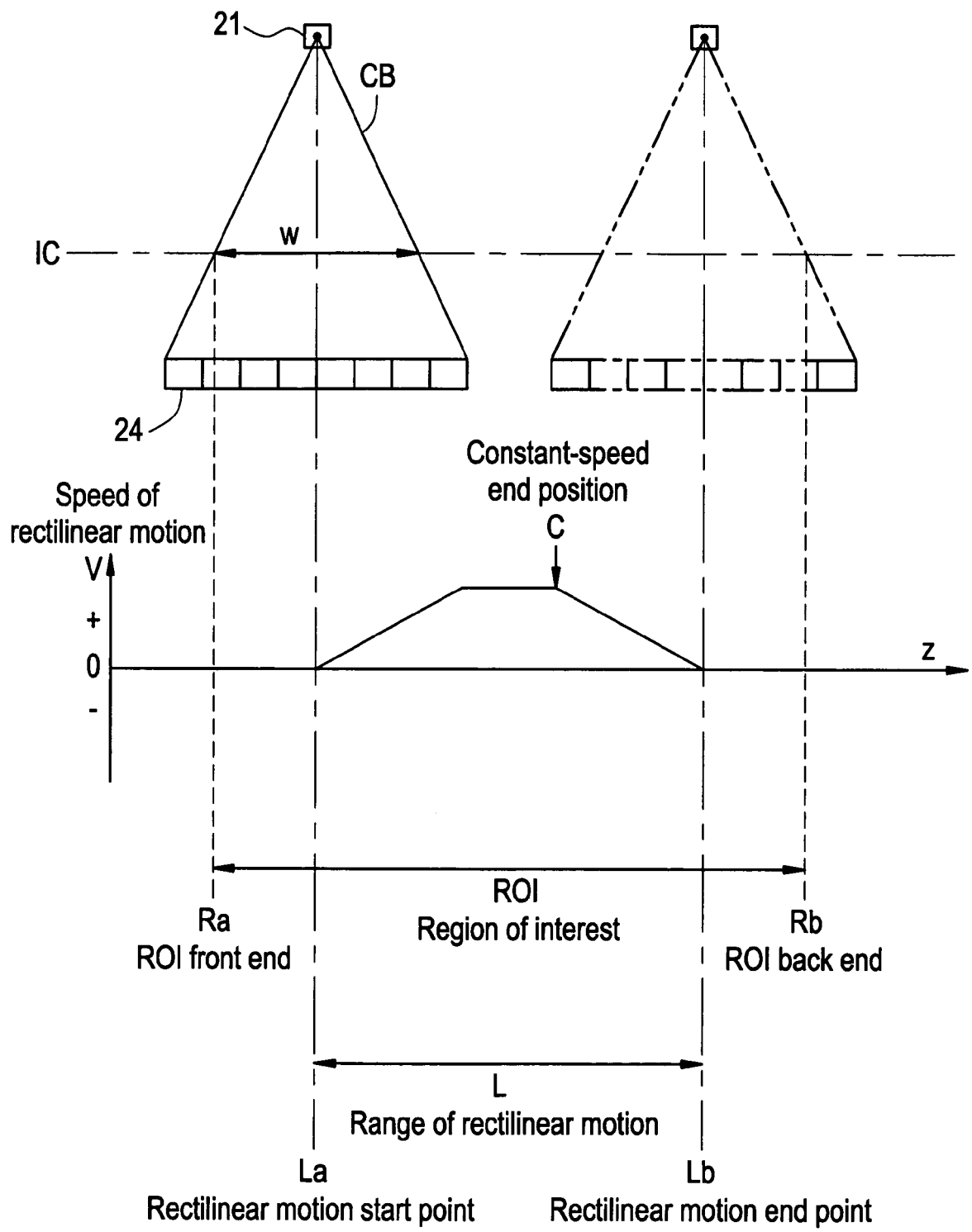
FIG. 28 is an explanatory diagram showing a region of interest and a range of rectilinear motion in Example 4.
Figure 29:
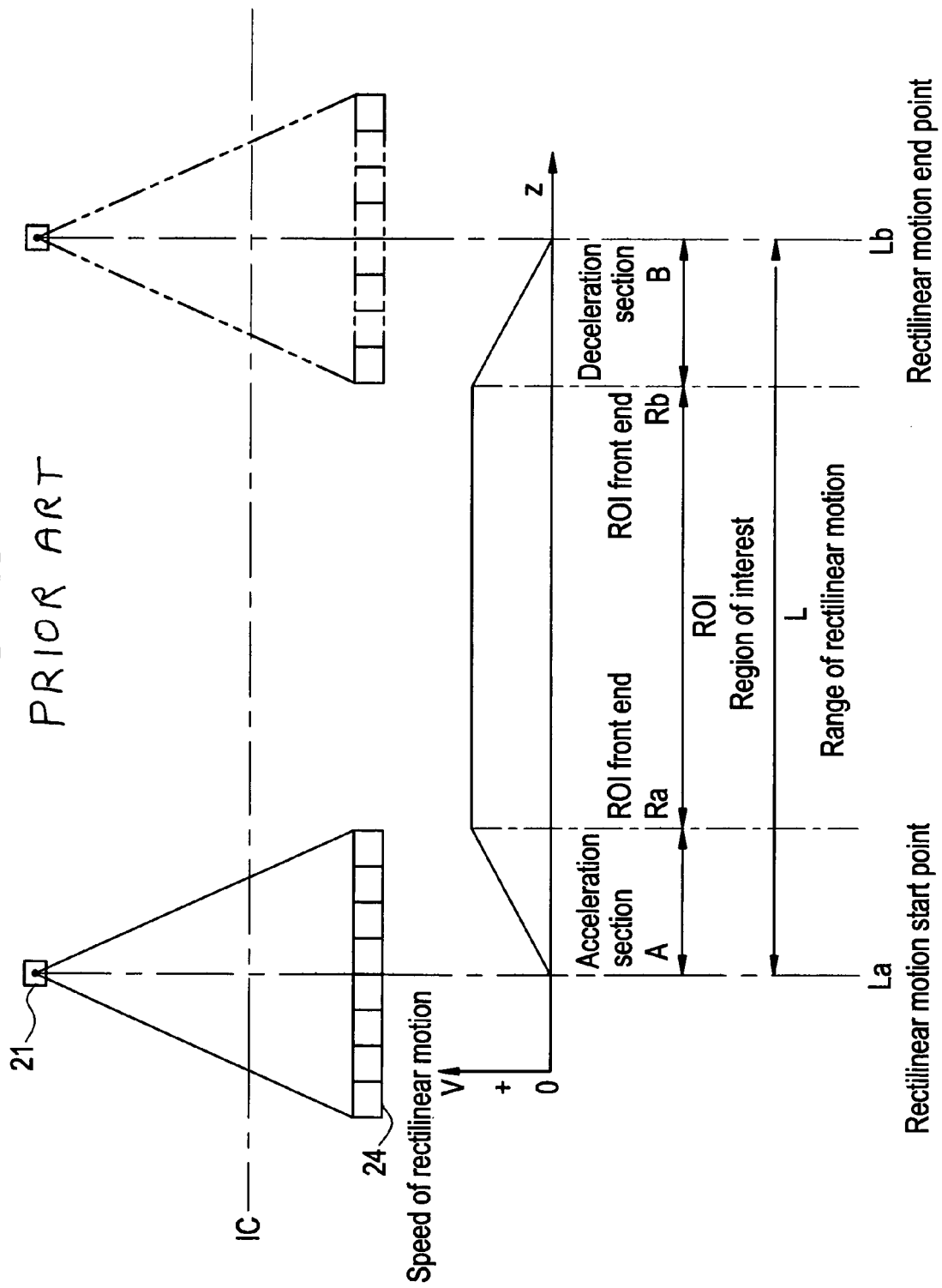
FIG. 29 is an explanatory diagram showing a region of interest and a range of rectilinear motion in the prior art.

As shown in FIG. 28, projection data are collected while rotating the X-ray tube 21 and multi-row detector 24 at the rectilinear motion start point La without rectilinearly moving the table 12, and a CT image is reconstructed using the collected projection data. Then, a contrast agent is injected into the subject to be imaged. This results in the CT image being changed by the contrast agent, and rectilinear motion of the table 12 is started based on the change.

According to the X-ray CT apparatus of Example 4, since a range of rectilinear motion L may be defined inside the region of interest ROI, the rectilinear motion start point La can be brought closer to the center of the region of interest ROI. Thus, the change in a CT image that triggers start of the rectilinear motion can be accurately ascertained. Therefore, the X-ray CT apparatus of Example 4 is especially well-suited for Smart Prep (GE) or Real Prep (Toshiba).

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT imaging method for conducting a helical scan for collecting projection data while making relative rotation of at least one of an X-ray tube and a multi-row detector around a subject to be imaged and making relative rectilinear motion of them with respect to the subject to be imaged, said method comprising the steps of:

defining a relative rectilinear motion start point and a relative rectilinear motion end point within a region of interest (ROI) for which a CT image is to be created;

collecting projection data from said relative rectilinear motion start point to said relative rectilinear motion end point;

producing a CT image at a desired image position in said region of interest using the collected projection data; and generating a first distance between the relative rectilinear motion start point and the relative rectilinear motion end point, wherein the relative rectilinear motion starts at the relative rectilinear motion start point and ends at the relative rectilinear motion end point; and generating a second distance between an ROI front end position and an ROI back end position, wherein the ROI starts at the ROI front end position and ends at the ROI back end position, and wherein the first distance is less than the second distance, wherein the X-ray tube generates an X-ray beam, wherein the relative rectilinear motion start point is located at a distance from the ROI front end position, wherein the distance is measured in a direction of the relative rectilinear motion and is equal to half of a thickness of the X-ray beam, and wherein the thickness is at a center of rotation of the X-ray tube and the multi-row detector.

2. The X-ray CT imaging method of claim 1, wherein said relative rectilinear motion end point lies inward from the ROI back end position by half or about half of a thickness of an X-ray beam in the direction of rectilinear motion.

3. The X-ray CT imaging method of claim 1, further comprising making reciprocal relative rectilinear motion by: making motion from said relative rectilinear motion start point to said relative rectilinear motion end point; then re-defining said relative rectilinear motion start point and said relative rectilinear motion end point as a new relative rectilinear motion end point and a new relative rectilinear motion start point, respectively; and making relative rectilinear motion in an opposite direction.

4. The X-ray CT imaging method of claim 1, further comprising the steps of: collecting projection data while making said relative rotation at said relative rectilinear motion start point; reconstructing a CT image using the collected projection data; and starting said relative rectilinear motion based on a change in said CT image.

5. The X-ray CT imaging method of claim 1, further comprising the step of: creating a CT image by a three-dimensional image reconstruction technique.

6. The X-ray CT imaging method of claim 5, wherein said three-dimensional image reconstruction technique is a three-dimensional backprojection method comprising: ordering the collected projection data based on the z-position of each view and extracting projection data corresponding to one line or a plurality of parallel lines at spacings of a plurality of pixels on an image reconstruction field; generating projection line data by multiplying said projection data by a cone beam reconstruction weight; generating image-positional line data by filtering said projection line data; determining backprojected pixel data of each pixel on the reconstruction field based on said image-positional line data; and determining backprojected data by adding the backprojected pixel data on a pixel-by-pixel basis for all views used in image reconstruction.

7. The X-ray CT imaging method of claim 1, further comprising measuring a position of the relative rectilinear motion along a z-axis.

8. The X-ray CT imaging method of claim 1, further comprising:

measuring a position of the relative rectilinear motion along a z-axis; and appending the z-position to the collected projection data.

9. The X-ray CT imaging method of claim 1, wherein the relative rectilinear motion start point is located within a boundary projected from the ROI.

10. An X-ray CT apparatus comprising:

an X-ray tube;

a multi-row detector;

a helical scanning device for collecting projection data while making relative rotation of at least one of said X-ray tube and said multi-row detector around a subject to be imaged and making relative rectilinear motion of them with respect to the subject to be imaged, from a relative rectilinear motion start point to a relative rectilinear motion end point defined within a region of interest (ROI) for which a CT image is to be created, wherein the relative rectilinear motion extends across a first distance between the relative rectilinear motion start point and the relative rectilinear motion end point, wherein the relative rectilinear motion starts at the relative rectilinear motion start point and ends at the relative rectilinear motion end point, wherein the ROI extends across a second distance from an ROI front end position to an ROI back end position, and wherein the first distance is less than the second distance, wherein the X-ray tube generates an X-ray beam, wherein the relative rectilinear motion start point is located at a distance from the ROI front end position, wherein the distance is measured in a direction of the relative rectilinear motion and is equal to half of a thickness of the X-ray beam, wherein the thickness is at a center of rotation of the X-ray tube and the multi-row detector; and an image reconstructing device for producing a CT image at a desired image position in said region of interest using the collected projection data.

11. The X-ray CT apparatus as defined by claim 10, wherein said relative rectilinear motion end point lies inward from the ROI back end position by half or about half of a thickness of an X-ray beam in the direction of rectilinear motion.

12. The X-ray CT apparatus of claim 10, wherein said helical scanning device collects the projection data while making reciprocal relative rectilinear motion by: making motion from said relative rectilinear motion start point to said relative rectilinear motion end point; then re-defining said relative rectilinear motion start point and said relative rectilinear motion end point as a new relative rectilinear motion end point and a new relative rectilinear motion start point, respectively; and making relative rectilinear motion in an opposite direction.

13. The X-ray CT apparatus of claim 10, wherein said helical scanning device collects projection data while making said relative rotation at said relative rectilinear motion start point, reconstructs a CT image using the collected projection data, and starts said relative rectilinear motion based on a change in said CT image.

14. The X-ray CT apparatus of claim 10, wherein said image reconstructing device creates a CT image by a three-dimensional image reconstruction technique.

15. The X-ray CT apparatus of claim 14, wherein said three-dimensional image reconstruction technique is a three-dimensional backprojection method comprising: ordering the collected projection data based on the z-position of each view and extracting projection data corresponding to one line or a plurality of parallel lines at spacings of a plurality of pixels on an image reconstruction field; generating projection line data by multiplying said projection data by a cone beam reconstruction weight; generating image-positional line data by filtering said projection line data; determining backprojected pixel data of each pixel on the reconstruction field based on said image-positional line data; and determining backprojected data by adding the backprojected pixel data on a pixel-by-pixel basis for all views used in image reconstruction.

16. An X-ray CT apparatus comprising:
an X-ray tube;
a multi-row detector;
an helical scanning device for collecting projection data from a relative rectilinear motion start point to a relative rectilinear motion end point while making relative rotation of at least one of said X-ray tube and said multi-row detector around a subject to be imaged and making relative rectilinear motion of them with respect to the subject to be imaged; and
an image reconstructing device for creating a CT image at a desired image position in a region of interest (ROI) from an ROI front end position anterior to said relative rectilinear motion start point to an ROI back end position posterior to said relative rectilinear motion end point using the collected projection data, wherein the relative rectilinear motion extends across a first distance between the relative rectilinear motion start point and the relative rectilinear motion end point, wherein the relative rectilinear motion starts at the relative rectilinear motion start point and ends at the relative rectilinear motion end point, wherein the ROI extends across a second distance from the ROI front end position to the ROI back end position, wherein the first distance is less than the second distance, wherein the X-ray tube generates an X-ray beam, wherein the relative rectilinear motion start point is located at a distance from the ROI front end position, wherein the distance is measured in a direction of the relative rectilinear motion and is equal to half of a thickness of the X-ray beam, and wherein the thickness is at a center of rotation of the X-ray tube and the multi-row detector.

17. The X-ray CT apparatus of claim 16, wherein said ROI back end position lies posterior to said relative rectilinear motion end point by half or approximately half of a thickness of an X-ray beam in the direction of rectilinear motion.

18. The X-ray CT apparatus of claim 16, wherein said helical scanning device collects the projection data while making reciprocal relative rectilinear motion by: making motion from said relative rectilinear motion start point to said relative rectilinear motion end point; then re-defining said relative rectilinear motion start point and said relative rectilinear motion end point as a new relative rectilinear motion end point and a new relative rectilinear motion start point, respectively; and making relative rectilinear motion in an opposite direction.

19. The X-ray CT apparatus of claim 16, wherein said helical scanning device collects projection data while making said relative rotation at said relative rectilinear motion start point, reconstructs a CT image using the collected projection data, and starts said relative rectilinear motion based on a change in said CT image.

* * * * *